United States Patent [19]
Miller et al.

[11] Patent Number: 5,858,353
[45] Date of Patent: *Jan. 12, 1999

[54] INSECT VIRUSES, SEQUENCES, INSECTICIDAL COMPOSITIONS AND METHODS

[75] Inventors: Lois K. Miller, Athens, Ga.; Bruce C. Black; Peter M. Dierks, both of Yardley, Pa.; Nancy C. Fleming, Rocky Hill, N.J.

[73] Assignees: American Cyanamid Company, Parsippany, N.J.; University of Georgia Research Foundation, Inc., Athens, Ga.

[*] Notice: The term of this patent shall not extend beyond the expiration date of Pat. No. 5,662,897.

[21] Appl. No.: 460,725

[22] Filed: Jun. 2, 1995

Related U.S. Application Data

[63] Continuation of Ser. No. 281,916, Jul. 27, 1994, Pat. No. 5,662,897.

[51] Int. Cl.[6] ............................. A61K 35/76; C12N 7/01; C12N 5/06; C07H 21/04
[52] U.S. Cl. .................. 424/93.6; 435/235.1; 435/320.1; 435/345; 536/23.1; 536/23.51
[58] Field of Search ............................ 424/DIG. 8, 93.6; 435/69.1, 91.4, 172.3, 235.1, 240.1, 320.1; 514/0.44; 536/23.1, 23.51

[56] References Cited

U.S. PATENT DOCUMENTS

| | | | |
|---|---|---|---|
| 5,180,581 | 1/1993 | Miller et al. | 424/93.2 |
| 5,246,936 | 9/1993 | Treacy et al. | 514/256 |
| 5,266,317 | 11/1993 | Tomalski et al. | 424/93.2 |
| 5,352,451 | 10/1994 | Miller et al. | 424/93.2 |
| 5,386,964 | 2/1995 | Mayo | 248/346.01 |

FOREIGN PATENT DOCUMENTS 2005658  6/1990  Canada .

OTHER PUBLICATIONS

O'Reilly and Miller (1991), "Improvement of a Baculovirus Pesticide by Deletion of the Egt Gene," *Biotechnology* 9: 1086–1089.

Kumar and Miller (1987), "Effects of Serial Passage of *Autographa californica*Nuclear Polyhedrosis Virus in Cell Culture," *Virus Research* 7: 335–349.

Lee and Miller (1978), "Isolation of Genotypic Variants of *Autographa californica*Nuclear Polyhedrosis Virus," *J. Virol.* 27: 754–767.

Gearing and Possee (1990), "Functional Analysis of a 603 Nucleotide Open Reading Frame Upstream of the Polyhedrin Gene of *Autographa californica*Nuclear Polyhedrosis Virus," *J. Gen. Virol.* 71: 251–262.

Passarelli and Miller (1993), "Three Baculovirus Genes Involved in Late and Very Late Gene Expressionn: ie–l, ie–n, and lef–2," *J. Virol.* 67: 2149–2158.

Vail et al. (1971), "Cross Infectivity of a Nuclear Polyhedrosis Virus Isolated from the Alfalfa Looper, *Autographa californica*," Proc. IV Int. Colloq. Insect Pathology, College Park, MD, pp. 297–304.

Possee et al., (1991), "Nucleotide Sequence of the *Autographa californica*Nuclear Polyhedrosis 9.4 kbp EcoRI–I and –R(Polyhedrin Gene) Region," *Virology*, 185: 229–241.

Croizier et al. (1988) "Recombination of *Autographa californica*and *Rachiplusia ou*Nuclear Polyhedrosis Viruses in *Galleria mellonella*L.," *J. gen. Virol.*69:177–185.

Possee et al. (1993) "Genetically Engineered Viral Insecticides: New Insecticides with Improved Phenotypes," *Pesticide Science*39:109–115.

*Primary Examiner*—Nancy Degen
*Assistant Examiner*—William Sandals
*Attorney, Agent, or Firm*—Greenlee, Winner and Sullivan, PC

[57] ABSTRACT

Insect viruses capable of killing at least one target insect pest quicker than previously described viruses and DNA sequence conferring that phenotype of faster killing are provided. Further improvement in the speed of killing is obtained when the virus of this invention also contains a nonfunctional egt gene to reduce feeding by the infected larvae, inhibit growth and further mediate the earlier death of the infected insect. A specifically exemplified faster-killing insect virus is the V-8 strain of AcMNPV. The faster killing phenotype is carried on a MluI to EspI fragment from 1.93 to 3.27 map units within the AcMNPV genome, and its sequence is provided herein as SEQ ID NO:3. V8vEGTDEL is the egt-inactivated derivative of AcMNPV V-8; the combination of the increased virulence of the V-8 genotype, for example, and the inactivation of the gene encoding ecdysteroid glycosyl transferase provides further improvement (as further decrease in time after infection until insect death). Additionally, such an EGT-deficient baculovirus may be still further modified to express a protein which affects ecdysis. Methods for producing the faster-killing insect virus, improved insecticidal compositions and improved methods of controlling insects are also included within the scope of this invention.

14 Claims, 11 Drawing Sheets

```
            MluI
L-1  2469  acgcgttccggcacgagctttgattgtaataagttttttacgaagcgatga  2518
           ||||||||||||||||||||||||||||||||||||||||||||||||||
V-8  2469  acgcgttccggcacgagctttgattgtaataagttttttacgaagcgatga  2518

L-1  2519  catgaccccgtagtgacaacgatcacgcccaaaagaactgccgactaca  2568
           ||||||||||||||||||||||||||||||||||||||||||||||||||
V-8  2519  catgaccccgtagtgacaacgatcacgcccaaaagaactgccgactaca  2568

L-1  2569  aaattaccgagtatgtcggtgacgttaaaactattaagccatccaatcga  2618
           ||||||||||||||||||||||||||||||||||||||||||||||||||
V-8  2569  aaattaccgagtatgtcggtgacgttaaaactattaagccatccaatcga  2618
                                                       *(lef-2)-->
L-1  2619  ccgttagtcgaatcaggaccgctggtgcgagaagccgcgaagtatggcga  2668
           ||||||||||||||||||||||||||||||||||||||||||||||||||
V-8  2619  ccgttagtcgaatcaggaccgctggtgcgagaagccgcgaagtatggcga  2668

L-1  2669  atgcatcgtataacgtgtggagtccgctcattagagcgtcatgtttagac  2718
           |||||||||||||||||||||||||||||||||| |||||||||||||||
V-8  2669  atgcatcgtataacgtgtggagtccgctcattagcgcgtcatgtttagac  2718

L-1  2719  aagaaagctacatatttaattgatcccgatgatttattgataaattgac  2768
           ||||||||||||||||||||||||||||||||||||||||||||||||||
V-8  2719  aagaaagctacatatttaattgatcccgatgatttattgataaattgac  2768

L-1  2769  cctaactccatacacggtattctacaatggcggggttttggtcaaaattt  2818
           ||||||||||||||||||||||||||||||||||||||||||||||||||
V-8  2769  cctaactccatacacggtattctacaatggcggggttttggtcaaaattt  2818

L-1  2819  ccggactgcgattgtacatgctgttaacggctccgcccactattaatgaa  2868
           ||||||||||||||||||||||||||||||||||||||||||||||||||
V-8  2819  ccggactgcgattgtacatgctgttaacggctccgcccactattaatgaa  2868

L-1  2869  attaaaaattccaattttaaaaaacgcagcaagagaaacatttgtatgaa  2918
           ||||||||||||||||||||||||||||||||||||||||||||||||||
V-8  2869  attaaaaattccaattttaaaaaacgcagcaagagaaacatttgtatgaa  2918

L-1  2919  agaatgcgtagaaggaaagaaaaatgtcgtcgacatgctgaacaacaaga  2968
           ||||||||  |||||||||||||||||||||||| |||||||||| ||||
V-8  2919  agaatgcgcagaaggaaagaaaaatgtcgttgacatgctgaacagcaaga  2968
```

FIG. 4A

```
L-1  2969  ttaatatgcctccgtgtataaaaaaaatattgaacgatttgaaagaaaac  3018
           ||||||||||||||||||||||||||||||||||  ||||||||||||||
V-8  2969  tcaatatgcctccgtgtataaaaaaatattgggcgatttgaaagaaaac  2018
                                           $----------------

L-1  3019  aatgtaccgcgcggcggtatgtacaggaagaggtttatactaaactgtta  3068
           ||||||||| |||||||||||||||||||||| ||||||  |||||||||
V-8  3019  aatgtacca cgcggcggtatgtacaggaagagatttatattaaactgtta  3068
              --------$ L-1  3069  cattgcaaacgtggtttcgtgtgccaagtgtgaaaaccgatgtttaatca  3118
           ||||||||||||||||||||||||||| ||||||||||||||||||||||
V-8  3069  cattgcaaacgtggtttcgtgtgccaaatgtgaaaaccgatgtttaatca  3118

L-1  3119  aggctctgacgcatttctacaaccacgactccaagtgtgtgggtgaagtc  3168
           | ||||||||  |||||||||||||||| |||||| ||||||||||||||
V-8  3119  atgctctga  gcatttctacaaccacgattccaaatgtgtgggtgaagtc  3168

L-1  3169  atgcatcttttaatcaaatcccaagatgtgtataaaccaccaaactgcca  3218
           ||||||||||||| ||||||||||||| || |||||||||||||||||||
V-8  3169  atgcatcttttaattaaatcccaagatgtttataaaccaccaaactgcca  3218

L-1  3219  aaaaatgaaaactgtcgacaagctctgtccgtttgctggcaactgcaagg  3268
           |||||||||||| |||||||  |||| || |||||||||||||||||||
V-8  3219  aaaaatgaaaaatgtcgacaagctttgcccgtttgctggcaactgcaagg  3268
                                HindIII

#(lef-2)
L-1  3269  gtctcaatcctatttgtaattattgaataataaaacaattataaatgcta  3318
           ||||||||||||||||||||||||||||||||||||||||||||||||||
V-8  3269  gtctcaatcctatttgtaattattgaataataaaacaattataaatgcta  3318

#(603 ORF)
L-1  3319  aatttgttttttattaacgatacaaaccaaacgcaacaagaacatttgta  3368
           ||||||||||||||||||||||||||||||||||||||||||||||||||
V-8  3319  aatttgttttttattaacgatacaaaccaaacgcaacaagaacatttgta  3368
                                                       MluI
L-1  3369  gtattatctataattgaaaacgcgtagttataatcgctgaggtaatattt  3418
           | |||||||||||||||||| || |||||||||     ||||||| |||
V-8  3369  gaattatctataattgaaaacgcataattataatcgtcaaggtaatgttt  3418
```

FIG.4B

| | | | |
|---|---|---|---|
| L-1 | 3419 | aaaatcattttcaaatgattcacagttaatttgcgacaatataatttttac | 3468 |
| | | ||||||||||||||||||||||||||||||||||||||||| |||||||| | | |
| V-8 | 3419 | aaaatcattttcaaatgattcacagttaatttgcgacagtataatttttgt | 3468 |

| | | | |
|---|---|---|---|
| L-1 | 3469 | tttcacataaactagacgcct.....tgtc.gtcttcttcttcgtattcc | 3512 |
| | | |||||||||||||||||||||    |||| ||| |||||||||||||| | |
| V-8 | 3469 | tttcacataaactagacgcctttatctgtctgtcgtcttcttcgtattct | 3518 |

| | | | |
|---|---|---|---|
| L-1 | 3513 | ttctcttttcattttctcctcataaaaattaacatagttattatcgta | 3562 |
| | | || ||||||||||||||||| ||||||||||| ||||| |||||||||| | |
| V-8 | 3519 | ttttcttttcattttctcttcataaaaattcacataattattatcgta | 3568 |

| | | | |
|---|---|---|---|
| L-1 | 3563 | tccatatatgtatctatcgtatagagtaaattttttgttgtcataaatat | 3612 |
| | | |||||||||||||| ||||| |||||||||||||||||||||||||||| | |
| V-8 | 3569 | tccatatatgtatctgtcgtaaagagtaaattttttgttgtcataaatat | 3618 |

| | | | |
|---|---|---|---|
| L-1 | 3613 | atatgtcttttttaatggggtgtatagtaccgctgcgcatagttttctg | 3662 |
| | | |||||||| |||||||||||||||||||||||||||||||||||||||| | |
| V-8 | 3619 | atatgttttttttaatggggtgtatagtaccgctgcgcatagttttctt | 3668 |

| | | | |
|---|---|---|---|
| L-1 | 3663 | taatttacaacagtgctattttctggtagttcttcggagtgtgttgcttt | 3712 |
| | | ||||||| | ||||||||||||||||| |||||||||||||||||||| | |
| V-8 | 3669 | taatttaaaccagtgctattttctggtaattcttcggagtgtgttgcttt | 3718 |

| | | | |
|---|---|---|---|
| L-1 | 3713 | aattattaaatttatataatcaatgaatttgggatcgtcggttttgtaca | 3762 |
| | | |||||||||||||||||||||||||||||||||||||||||||||||||| | |
| V-8 | 3719 | aattattaaatttatataatcaatgaatttgggatcgtcggttttgtaca | 3768 |

NaeI
| | | | |
|---|---|---|---|
| L-1 | 3763 | atatgttgccggcatagtacgcagcttcttcta................ | 3795 |
| | | |||||||||||||||||||||||||||    |||| | |
| V-8 | 3769 | atatgttgccggcatagtacgcagctggctctaaatcaatattttttaaa | 3818 |

| | | | |
|---|---|---|---|
| L-1 | 3796 | .........gttcaattacaccattttttagcagcaccggattaacataa | 3836 |
| | |   | |||    |||||||||||| ||| |||||||||||| | |
| V-8 | 3819 | caacgactggatcaacattaccattttttagcaacactggattaacataa | 3868 |

| | | | |
|---|---|---|---|
| L-1 | 3837 | ctttccaaaatgttgtacgaaccgttaaacaaaaacagttcacctcccctt | 3886 |
| | | |||||||||| |||||||| |||| |||||||||||||||||||| || | |
| V-8 | 3869 | ttttccaaaatgctgtacgaagcgtttaacaaaaacagttcacttccgtt | 3918 |

FIG.4C

```
                                                      <--
L-1  3887  ttctatactattgtctgcgagcagttgtttgttgttaaaaataacagcca  3936
           ||||||||||| |||||||||||||| |||||||||||||||| ||||
V-8  3919  ttctatactatcgtctgcgagcagttgcttgttgttaaaaataacggcca  3968

*(603 ORF)
L-1  3937  ttgtaatgagacgcacaaactaatatcacaaactggaaatgtctatc...  3983
           ||||||||| ||||||||||||||||| ||| ||| |||  ||||||
V-8  3969  ttgtaatgaaacgcacaaactaatattacacactaaaaaaatctatcatt  4018

EcoRV
L-1  3984  .......aatatatagttgctgatatcatggagataattaaaatgataac  4026
                  ||||||||||||||||| ||| | ||||||||||||||||||
V-8  4019  tcggcttaatatatagttgctgatattatgtaaataattaaaatgataac  4068

L-1  4027  catctcgcaaataaataagtattttactgttttcgtaacagttttgtaat  4076
           ||||||||||||||||||||||||||||||||||||||||||||||||||
V-8  4069  catctcgcaaataaataagtattttactgttttcgtaacagttttgtaat  4118

*(polh)-->
L-1  4077  aaaaaaacctataaatatgccggattattcataccgtcccaccatcgggc  4126
           ||||||||||||||||||||||||||||||||||||||||||||||||||
V-8  4119  aaaaaaacctataaatatgccggattattcataccgtcccaccatcgggc  4168

L-1  4127  gtacctacgtgtacgacaacaagtactacaaaaatttaggtgccgttatc  4176
           |||||||||||||||||||||||||| || ||||||||||||||||||||
V-8  4169  gtacctacgtgtacgacaacaaatattacaaaaatttaggtgccgttatc  4218

EspI
L-1  4177  aagaacgctaagc  4189
           |||||||||||||
V-8  4219  aagaacgctaagc  4231
```

FIG.4D

```
L-1    1   MANASYNVWSPLIRASCLDKKATYLIDPDDFIDKLTLTPYTVFYNGGVLV    50
           ||||||||||||.||||||||||||||||||||||||||||||||||||
V-8    1   MANASYNVWSPLISASCLDKKATYLIDPDDFIDKLTLTPYTVFYNGGVLV    50

L-1   51   KISGLRLYMLLTAPPTINEIKNSNFKKRSKRNICMKECVEGKKNVVDMLN   100
           |||||||||||||||||||||||||||||||||||||.||||||||||||
V-8   51   KISGLRLYMLLTAPPTINEIKNSNFKKRSKRNICMKECAEGKKNVVDMLN   100

********
L-1  101   NKINMPPCIKKILNDLKENNVPRGGMYRKRFILNCYIANVVSCAKCENRC   150
           .||||||||||.||||||||||||||||||||||||||||||||||||||
V-8  101   SKINMPPCIKKILGDLKENNVPRGGMYRKRFILNCYIANVVSCAKCENRC   150

L-1  151   LIKALTHFYNHDSKCVGEVMHLLIKSQDVYKPPNCQKMKTVDKLCPFAGN   200
           ||.||||||||||||||||||||||||||||||||||||.|||||||||
V-8  151   LINALTHFYNHDSKCVGEVMHLLIKSQDVYKPPNCQKMKNVDKLCPFAGN   200

L-1  201   CKGLNPICNY   210
           ||||||||||
V-8  201   CKGLNPICNY   210
```

FIG.5

```
GTCGACGCGC TTCTGCCTAT AATTGCACAC TAACATGTTG CCCTTTGAAC TTGACCTCGA TTGTGTTAAT
TTTTGGCTAT AAAAAGGTCA CCCTTTAAAA TTTGTTACAT AATCAAATTA CCAGTACAGT TATTCGGTTT
           atg
GAAGCAAAAT GACTATTCTC TGCTGGCTTG CACTGCTGTC TACGCTTACT GCTGTAAATG CGGCCAATAT
EGTDEL1
─────────▶
ATTGGCCGTG TTTCCTACGC CAGCTTACAG CCACCATATA GTGTACAAAG TGTATATTGA AGCCCTTGCC
GAAAAATGTC ACAACGTTAC GGTCGTCAAG CCCAAACTGT TGCCGTATTC AACTAAAACT TATTGCGGTA
                                                             EcoRI
ATATCACGGA AATTAATGCC GACATGTCTG TTGAGCAATA CAAAAAACTA GTGGCGAATT CGGCAATGTT
TAGAAAGCGC GGAGTGGTGT CCGATACAGA CACGGTAACC GCCGCTAACT ACCTAGGCTT GATTGAAATG
TTCAAAGACC AGTTTGACAA TATCAACGTG CGCAATCTCA TTGCCAACAA CCAGACGTTT GATTTAGTCG
TCGTGGAAGC GTTTGCCGAT TATGCGTTGG TGTTTGGTCA CTTGTACGAT CCGGCGCCCG TAATTCAAAT
CGCGCCTGGC TACGGTTTGG CGGAAAACTT TGACACGGTC GGCGCCGTGG CGCGGCACCC CGTCCACCAT
CCTAACATTT GGCGCAGCAA TTTCGACGAC ACGGAGGCAA ACGTGATGAC GGAAATGCGT TTGTATAAAG
AATTTAAAAT TTTGCCCAAC ATGTCCAACG CGTTGCTCAA ACAACAGTTT GGACCCAACA CACCGACAAT
TGAAAAACTA CGCAACAAGG TGCAATTGCT TTTGCTAAAC CTGCATCCCA TATTTGACAA CAACCGACCC  Δ1094 bp
GTGCCGCCCA GCGTGCAGTA TCTTGGCGGA GGAATCCATC TTGTAAAGAG CGCGCCCGTTG ACCAAATTAA
GTCCGGTCAT CAACGCGCAA ATGAACAAGT CAAAAAGCGG AACGATTTAC GTAAGTTTTG GGTCGAGCAT
TGACACCAAA TCGTTTGCAA ACGAGTTTCT TTACATGTTA ATCAATACGT TCAAAACGTT GGATAATTAC
ACCATATTAT GGAAAATTGA CGACGAAGTA GTAAAAAACA TAACGTTGCC CGCCAACGTA ATCACGCAAA
ATTGGTTTAA TCAACGCGCC GTGCTGCGTC ATAAAAAAAT GGCGGCGTTT ATTACGCAAG GCGGACTACA
ATCGAGCGAC GAGGCCTTGG AAGCCGGGAT ACCCATGGTG TGTCTGCCCA TGATGGGCGA CCAGTTTTAC
CATGCGCACA AATTACAGCA ACTCGGCCTA GCCCGCGCCT TGGACACTGT TACCGTTTCC AGCGATCAAC
TACTAGTGGC GATAAACGAC GTGTTGTTTA ACGCGCCTAC CTACAAAAAA CACATGGCCG AGTTATATGC
                                                  XbaI
GCTCATCAAT CATGATAAAG CAACGTTTCC GCCTCTAGAT AAAGCCATCA AATTCACAGA ACGCGTAATT
CGATATAGAC ATGACATCAG TCGTCAATTG TATTCATTAA AAACAACAGC TGCCAATGTA CCGTATTCAA
                                                                      ◀─────
                                                                      EGTDEL2
                                                                      taa
ATTACTACAT GTATAAATCT GTGTTTTCTA TTGTAATGAA TCACTTAAGA CACTTTTAAT TACGTCAATA
AATGTTATTC ACCATTATTT ACCTGGTTTT TTTGAGAGGG GCTTTGTGCG ACTGCGCACT TCCAGCCTTT
ATAAACGCTC ACCAACCAAA GCAGGTCATT ATTGTGCCAG GACGTTCAAA GGCGAAACAT CGAAATGGAG
TCTGTTCAAA CGCGCTTATG TGCCAGTAGC AATCAATTTG CTCCGTTCAA AAAGCGCCAG CTTGCCGTGC
CGGTCGGTTC TGTGAACAGT TTGACACACA CCATCACCTC CACCACCGTC ACCAGCGTGA TTCCAAAAAA
TTATCAAGAA AAACGTCAGA AAATATGCCA CATAATATCT TCGTTGCGTA ACACGCACTT GAATTTCAAT
AAGATACAGT CTGTACATAA AAAGAAACTG CGGCATTTGC AAAATTTGCT AAGAAAAAAG AACGAAATTA
TTGCCGAGTT GGTTAGAAAA CTTGAAAGTG CACAGAAGAA GACAACGCAC AGAAATATTA GTAAACCAGC
```

FIG.6A

```
TCATTGGAAA TACTTTGGAG TAGTCAGATG TGACAACACA ATTCCCACAA TTATTGGCAA CGAAAAGTTT
GTAAGGAGAC GTTTGGCCGA GCTGTGCACA TTGTACAACG CCGAGTACGT GTTTTGCCAA GCACGCGCCG
ATGGAGACAA AGATCGACAG GCACTAGCGA GTCTGCTGAC GGCGGCGTTT GGTTCGCGAG TCATAGTTTA
TGAAAATAGT CGCCGGTTCG AGTTTATAAA TCCGGACGAG ATTGCTAGTG GTAAACGTTT AATAATTAAA
CATTTGCAAG ATGAATCTCA AAGTGATATT AACGCCTATT AATTTGAAAG GTGAGGAAGA GCCCAATTGC
GTTGAGCGCA TTACCATAAT GCCATGTATT TTAATAGATA CTGAGATCTG TTTAAATGTC AGATGCCGTT
CTCCTTTTGC CAAATTCAAA GTATTGATTA TTGTAGATGG CTTTGATAGC GCTTATATTC AGGCTACCTT
TTGTAGCATT AGCGATAGTG TAACAATTGT TAACAAATCT AACGAAAAGC ATGTAACGTT TGACGGGTTT
GTAAGGCCGG ACGATGAAGG TACAACAATG CCTTATGTCA TTGGACCATT ATATTCTGTC GAC
```

FIG.6B

```
E2     TGAGACGCACAAACTAATATCACAAACTGGAAATGTCTATCA---------ATATATAG
V8     TGAAACGCACAAACTAATATTACACACTAAAAATGTCTATCATTTCGGCTTAATATATAG
V1000  TGAAACGCACAAACTAATATTACACACTAAAAAAATCTATCATTTCGGCTTAATATATAG

E2     TTGCTGATATCATGGAGATAATTAAAATGATAACCATCTCGCAAATAAATAAGTATTTTA
V8     TTGCTGATATTATGTAAATAATTAAAATGATAACCATCTCGCAAATAAATAAGTATTTTA
V1000  TTGCTGATATTATGTAAATAATTAAAATGATAACCATCTCGCAAATAAATAAGTATTTTA

E2     CTGTTTTCGTAACAGTTTTGTAATAAAAAAACCTATAAAT ATG CCG GAT TAT TCA
V8     CTGTTTTCGTAACAGTTTTGTAATAAAAAAACCTATAAAT ATG CCG GAT TAT TCA
V1000  CTGTTTTCGTAACAGTTTTGTAATAAAAAAACCTATAAAT ATG CCG GAT TAT TCA

E2     TAC CGT CCC ACC ATC GGG CGT ACC TAC GTG TAC GAC AAC AAG TAC
V8     TAC CGT CCC ACC ATC GGG CGT ACC TAC GTG TAC GAC AAC AAA TAT
V1000  TAC CGT CCG ACC ATC GGG CGT ACC TAC GTG TAC GAC AAC AAA TAT

E2     TAC AAA AAT TTA GGT GCC GTT ATC AAG AAC GCT AAG CGC AAG AAG
V8     TAC AAA AAT TTA GGT GCC GTT ATC AAG AAC GCT AAG CGC AAG AAG
V1000  TAC AAA AAC TTG GGT TCT GTT ATT AAA AAC GCC AAG CGC AAG AAG

E2     CAC TTC GCC GAA CAT GAG ATC GAA GAG GCT ACC CTC GAC CCC CTA
V8     CAC TTC GCC GAA CAT GAG ATC GAA GAG GCT ACC CTC GAC CCC CTA
V1000  CAC CTA ATC GAA CAT GAA GAA GAG AAG NAC TTG GAT CCC TTA

E2     GAC AAC TAC CTA GTG GCT GAG GAT CCT TTC CTG GGA CCC GG
V8     GAC AAC TAC CTA GTG GCT GAG GAT CCT TTC CTG GGA CCC GG
V1000  GAC AAT TAC ATG GTT GCC NNA GAT CCT TTT CTA GGA CCT GG
```

FIG.7

INSECT VIRUSES, SEQUENCES, INSECTICIDAL COMPOSITIONS AND METHODS

This application is a Continuation of U.S. Pat. application Ser. No. 08/281,916, filed Jul. 27, 1994 now U.S. Pat. No. 5,662,897.

TECHNICAL FIELD

The present invention relates to methods and compositions using baculoviruses and sequences therefrom for improved biological control of insect pests. More particularly, the present invention relates to a recombinant baculovirus which has improved properties in insect control and the segment therefrom conferring improved properties, i.e., more rapid death for at least one target insect. The present invention also relates to genetically modified baculoviruses with further improved killing properties and methods of use.

BACKGROUND OF THE INVENTION

Interest in the biological control of insect pests has arisen as a result of disadvantages of conventional chemical pesticides. Chemical pesticides generally affect beneficial as well as nonbeneficial species. Insect pests tend to acquire resistance to such chemicals so that new insect pest populations can rapidly develop that are resistant to these pesticides. Furthermore, chemical residues pose environmental hazards and possible health concerns. Biological control presents an alternative means of pest control which can reduce dependence on chemical pesticides.

The primary strategies for biological control include the deployment of naturally-occurring organisms which are pathogenic to insects (entomopathogens) and the development of crops that are more resistant to insect pests. Approaches include the identification and characterization of insect genes or gene products which may serve as suitable targets for insect control agents, the identification and exploitation of previously unused microorganisms (including the modification of naturally-occurring nonpathogenic microorganisms to render them pathogenic to insects), the modification and refinement of currently used entomopathogens, and the development of genetically engineered crops which display greater resistance to insect pests.

Viruses that cause natural epizootic diseases within insect populations are among the entomopathogens which have been developed as biological pesticides. Baculoviruses are a large group of viruses which infect only arthropods (Miller, L. K. (1981) in *Genetic Engineering in the Plant Sciences*, N. Panopoulous, (ed.), Praeger Publ., New York, pp. 203–224; Carstens, (1980) *Trends in Biochemical Science* 52:107–110; Harrap and Payne (1979) in *Advances in Virus Research*, Vol. 25, Lawfer et al. (eds.), Academic Press, New York, pp. 273–355; *The Biology of Baculoviruses*, Vol. I and II, Granados and Federici (eds.), CRC Press, Boca Raton, Fla., 1986). Many baculoviruses infect insects which are pests of commercially important agricultural and forestry crops. Such baculoviruses are potentially valuable as biological control agents. Four different baculoviruses have been registered for use as insecticides by the U.S. Environmental Protection Agency. Among the advantages of baculoviruses as biological pesticides is their host specificity. Not only do baculoviruses as a group infect only arthropods, but also individual baculovirus strains usually only infect one or a few species of insects. Thus, they pose no risk to man or the environment, and can be used without adversely affecting beneficial insect species.

Baculoviruses, including AcMNPV, have been found in approximately 400 different species across several different insect orders; the vast majority of these viruses occur in the order Lepidoptera. Baculoviruses are known to infect insects in both natural ecosystems (e.g., forests and prairies) and monocultural agro-ecosystems (e.g., cotton fields).

*Autographa californica* nuclear polyhedrosis virus, (AcMNPV) is the most extensively characterized baculovirus known. AcMNPV belongs to the family Baculoviridae, subfamily Eubaculovirinae, genus Nuclear Polyhedrosis Virus, and the subgenus Multiple Nucleocapsid Virus, which are characterized by the formation of viral occlusion bodies (or polyhedra) in the nuclei of infected host cells. The virus was first isolated more than 20 years ago from an alfalfa looper, *Autographa californica*, during a naturally occurring epizootic infection in California. Since then, the virus has been characterized extensively using biochemical and molecular techniques, and extensive DNA sequence within the 128 kbp genome is known. AcMNPV has been designated as the type species for the subgenus Multiple Nucleocapsid Virus.

Baculovirus subgroups include nuclear polyhedrosis viruses (NPV), granulosis viruses (GV), and non-occluded baculoviruses. In the occluded forms of baculoviruses (GV and NPV), the virions (enveloped nucleocapsids) are embedded in a crystalline protein matrix. This structure, referred to as an inclusion or occlusion body, is the form found extraorganismally in nature and is responsible for spreading the infection between organisms. The characteristic feature of the NPVs is that many virions are embedded in each occlusion body. The NPV occlusion bodies are relatively large (up to 5 micrometers). Occlusion bodies of the GV viruses are smaller and contain a single virion each. The crystalline protein matrix of the occlusion bodies of both forms is primarily composed of a single 25,000 to 33,000 dalton polypeptide which is known as polyhedrin or granulin. Baculoviruses of the non-occluded subgroup do not produce a polyhedrin or granulin protein, and do not form occlusion bodies.

In nature, infection is initiated when an insect ingests food contaminated with baculovirus particles, typically in the form of occlusion bodies for an NPV such as AcMNPV. The occlusion bodies dissociate under the alkaline conditions of the insect midgut, releasing individual virus particles which then invade epithelial cells lining the gut. Within a host cell, the baculovirus migrates to the nucleus where replication takes place. Initially, certain specific viral proteins are produced within the infected cell via the transcription and translation of so-called "early genes." Among other functions, these proteins are required to allow replication of the viral DNA, which begins 4 to 6 hours after the virus enters the cell. Extensive viral DNA replication proceeds up to about 24 hours post-infection (pi). From about 8 to 20 hours pi, the infected cell produces large amounts of "late viral gene products." These include components of the nucleocapsid which surrounds the viral DNA during the formation of progeny virus particles. Production of the progeny virus particles begins around 12 hours pi. Initially, progeny virus migrate to the cell membrane where they acquire an envelope as they bud out from the surface of the cell. This non-occluded virus can then infect other cells within the insect. Polyhedrin synthesis begins about 18 hours after infection and increases to very high levels by 24 hours pi. At that time, there is a decrease in the number of budded virus particles, and progeny virus are then embedded in occlusion bodies. Occlusion body formation continues until the cell dies or lyses. Some baculoviruses infect virtually every tissue in the host insect so that at the end of the infection process, the entire insect is liquified, releasing extremely large numbers of occlusion bodies which can then spread the infection to other insects. (Reviewed in *The Biology of Baculoviruses*, Vol. I and II, Granados and Federici (eds.), CRC Press, Boca Raton, Fla., 1986.)

Larvae become increasingly resistant to viral infection as they grow and mature. Both adult tissues and pupal tissues appear to be refractory to viral infection. The primary means of infection by AcMNPV appears to be via horizontal transmission. Insects typically acquire AcMNPV by consuming contaminated food. The occlusions dissolve in the insect mid-gut and release virions which establish a primary site of infection in mid-gut cells.

The ability of AcMNPV to persist and spread in the environment is governed by many interrelated factors (reviewed by Evans, H. (1986) *The Biology of Baculoviruses, Ecology and Epizoology of Baculoviruses*, Granados, R. R. and Federici, B. A. (eds.) pp.89–132). Factors such as the relative sensitivity of the insect host to virus, as well as developmentally determined sensitivity to AcMNPV, are important. Host density also appears to play an important role in determining persistence and spread of baculoviruses. There are important implications concerning the role of biotic and abiotic forces that determine AcMNPV environmental transmission and persistence. For example, predators compete with virus for available insect hosts and tend to reduce potential virus productivity by removal of these virus-susceptible hosts from the environment. On the other hand, predators can also indirectly increase the survival capacity and spread of MNPVs by increasing virus dispersal and by making more efficient use of available host populations. This predator-aided transmission is generally by passage of infectious MNPVs through the gut of predatory insects, birds, and mammals. Likewise, abiotic factors (such as ultraviolet (UV) light, rainfall, temperature, and pH) have a major influence on virus survival and spread in the environment. For example, baculoviruses appear to be particularly sensitive to UV irradiation and to alkaline pH. Persistence of field applied virus without UV protection can be as little as 1–2 days in the field. Soil appears to be a particularly important reservoir for persistence of baculoviruses. The decline of viruses in the soil is slow and wide range of times for persistence and viability have been reported. The ubiquitous and harmless association between baculoviruses and humans and other species due to dietary exposure underscores their safety and value as insecticides.

One potential disadvantage to using baculoviruses as pesticides is the length of time between virus ingestion and insect death. During this time, the pest insect continues to feed and damage crops. Because pesticides are generally applied only after an infestation is apparent, it is critical that the time of feeding be minimized. One approach to lessening insect feeding time in insect control via viral infection is the use of ecdysteroid glycosyl transferase-deficient baculovirus (O'Reilly and Miller (1991) *Biotechnology* 9:1086–1089; U.S. Pat. No. 5,180,581, Miller and O'Reilly; U.S. Pat. No. 5,352,451, issued Oct. 4, 1994, all of which are incorporated by reference). Other approaches include the insertion of genes encoding insect toxins or hormones into the viral genome (Hammock et al. (1993) *Arch. Insect Biochem. Physiol.* 22:315–344; McCutchen et al. (1991) *Bio/Technology* 9:848–852; Tomalski and Miller (1991) *Nature* 352:82–85; Tomalski and Miller (1992) *Bio/Technology* 10:545–549 and Stewart et al. (1991) *Nature* 352:85–88). Another approach is the incorporation of an insect-specific paralytic neurotoxin gene into a baculovirus genome (see, e.g., U.S. Pat. No. 5,266,317, issued Nov. 30, 1993, Tomalski and Miller, which discloses insect-predacious mite toxins; U.S. Pat. application Ser. No. 08/009,625, filed Jan. 29, 1993 now U.S. Pat. No. 5,386,964; Canadian Patent Application 2,005,658, Zlotkin et al.; Zlotkin et al. (1971) *Toxicon* 9:1–8, which disclose *Androctonus australis* toxin sequences).

There is a need for biological pesticides, specifically insect viruses, which reduce feeding by the insect before death and/or which result in a shorter time between infection and death when compared to prior art insect viruses. A biological pesticide is preferred because it creates less of an environmental hazard than a chemical pesticide. The exploitation of a recombinant virus which results in more rapid insect killing than available viruses will allow improved biological control of insect pests.

SUMMARY OF THE INVENTION

This invention specifically provides a purified and isolated recombinant baculovirus (called AcMNPV V-8 herein) which has improved killing properties as compared with prior art *Autographa californica* Nuclear Polyhedrosis Virus strains, against at least one insect pest including, but not limited to, *Spodoptera frugiperda*. The object baculovirus has been deposited with the American Type Culture Collection as ATCC VR-2465 (American Type Culture Collection, 12301 Parklawn Drive, Rockville, Md.). Improved killing properties against at least one insect pest means that when at least one species of insect pest is infected, the time between infection and insect death is shorter than with a comparison AcMNPV, e.g., AcMNPV E2 (ATCC VR-1344).

A further specific object of the present invention is an AcMNPV V-8 derivative which has been genetically engineered to inactivate the gene encoding ecdysteroid glycosyltransferase (egt). A preferred embodiment is V8vEGTDEL, which is the AcMNPV V8 derivative in which a portion of egt is deleted, with the result that a functional ecdysteroid glucosyltransferase is not produced during the viral infection process.

An additional object of the present invention is a segment of insect virus DNA which confers the improved (i.e., faster) killing phenotype when incorporated in the genome of a heterologous insect virus. As specifically exemplified such a DNA fragment is the MluI to EspI fragment from the region of the AcMNPV V-8 genome of 1.93 to 3.27 map units (or from the V1000 nuclear polyhedrosis virus, which appears to be closely related to or identical to *Rachiplusia ou* Nuclear Polyhedrosis Virus); the DNA sequence of the exemplified V-8 fragment is given in FIGS. 4A–4D (SEQ ID NO:3). This DNA segment carries sequences encoding a late expression factor (lef-2), and polypeptide of 603 amino acids (function unknown) and sequences upstream of the polyhedrin gene. Within this MluI to EspI fragment of the V-8 is a smaller region which is capable of conferring the improved killing phenotype when incorporated into the genome of a (recombinant) AcMNPV; this smaller region is between nucleotide 3026 and 4231 (V-8 sequence) of FIG. 4, which corresponds to nucleotides 194–826 of SEQ ID NO:3. Also within the scope of the invention are other recombinant insect viruses, including baculoviruses, in which such a DNA fragment conferring the improved killing phenotype has been incorporated into the genome with the result that at least one insect pest is killed quicker after infection than the corresponding baculovirus which has not been so genetically engineered or which otherwise does not contain a related heterologous DNA segment which confers increased virulence.

The present invention also provides methods for improving the killing properties of a baculovirus by introducing a segment of DNA conferring a phenotype of improved killing, e.g., faster insect death of at least one species of insect pest after infection, e.g., and by confirming the improved killing property by determining that the $LT_{50}$ (time required for killing 50% of test larvae at a standard virus dose, using a dose killing 90% of test larvae by set time post infection) is shorter for the genetically engineered strain than for the parental baculovirus. The genetically engineered strain may be produced by molecular biological techniques using an insect virus selected from the group consisting of nuclear polyhedrosis viruses including, but not limited to, *Lymantria dispar* NPV, *Autographa californica* NPV, *Synographa falcifera* NPV, *Spodoptera lituralis* NPV, *Spodoptera exigua* NPV, *Spodoptera frugiperda* NPV, *Heliothis armigera* NPV, *Mamestra brassicae* NPV, *Choristoneura fumiferana* NPV, *Trichoplusia ni* NPV, *Helicoverpa zea* NPV and *Manduca sexta* NPV; granulosis viruses including, but not limited to, *Cydia pomonella* GV, *Pieris brassicae* GV and *Trichoplusia ni* GV. Non-occluded viruses from the Baculovirinae may also be genetically modified to improve their killing properties for particular target insects; examples of such non-occluded baculovirinae include, but are not limited to, those of *Orcytes rhinoceros* and *Heliothis zea* non-occluded baculovirinae. Functionally equivalent sequences conferring improved killing properties may be isolated from viruses other than as specifically exemplified herein, and incorporated into viral genomes which do not naturally contain them to produce insect viruses with improved insect control properties.

Alternatively it may be produced by co-infection of a first baculovirus with a second baculovirus whose genome comprises said DNA fragment, wherein said first and second baculoviruses are sufficiently related (i.e., have sufficient DNA sequence identity at least over limited distances on regions flanking the sequences conferring the improved killing phenotype) so that recombination occurs to result in a recombinant baculovirus being produced which incorporates the DNA conferring the improved killing phenotype.

Further objects of the present invention are insecticidal compositions comprising the baculoviruses with improved killing properties against at least one insect pest. Preferred viruses include V8vEGTDEL, AcMNPV V-8, vEcoRIhybI, vEcoRIHybIFS and nuclear polyhedrosis viruses and granulosis viruses and non-occluded baculovirinae viruses in a non-limiting fashion as set forth herein above into which a segment of DNA conferring the improved killing phenotype has been genetically engineered or incorporated by recombination. Preferred insecticidal compositions of the present invention are formulated as wettable powders. The composition of a preferred wettable powder insecticidal composition is as follows:

| Ingredient | Nominal Percent (w/w) |
|---|---|
| V8vEGTDEL polyhedrin inclusion bodies | 10.0% |
| MORWET D425 | 30.0% |
| MOREWET EFW | 20.0% |
| Kaolin Clay | 16.0% |
| MICROCEL E | 16.0% |
| UV-9 oxybenzone or charcoal | 5.0% |
| EUDRAGIT S100 | 2.0% |
| Citric Acid | 0.9% |
| polyethylene glycol MW400 | 0.1% |

Optionally, a stilbene brightener can be added to the formulation to enhance infectivity or potentiate the insecticidal effects of the insect virus.

The preferred composition described above is formulated as follows:
 a) preparing an aqueous suspension of EUDRAGIT S100 (1% w/v);
 b) dissolving the EUDRAGIT S100 by adding the pH of the suspension of step (a) to 9.0 to 9.5;
 c) adding viral PIBs and UV-9 oxybenzone or charcoal to the solution of step (b), and blending to produce an even suspension;
 d) air drying the even suspension of step (c);
 e) milling the dried material of step (d) to produce milled material; and
 f) dry blending the milled material of step (e) with MORWET D425, MOREWET EFW wetting agent, Kaolin Clay as a bulking agent, MICROCELL E as a flow agent, citric acid and polyethylene glycol MW400 to provide flexibility to the milled material.

BRIEF DESCRIPTION OF THE DRAWINGS

FIG. 3A is the map for the AcMNPV L-1 wild type (thin line represents L-1 DNA). FIG. 3B is the map of AcMNPV V-8 (thick line represents V-8 DNA). The extra HindIII site in lef-2 is one distinguishing (physical) characteristic of V-8. V-8 is missing both the MluI site within the 603 ORF and the EcoRV site between the 603 ORF and polh. The V-8 603 ORF has a premature stop codon generated by an insertion and is predicted to produce an incomplete, non-functional polypeptide product (note "X" through the 603 ORF). FIG. 3C is the map of vEcoRIHybI recombinant virus containing the portion of the V-8 genome indicated by the thick bar. Although the transfer plasmid used to construct this hybrid contained V-8 sequence to the MluI site at 1.93 m.u., allelic replacement limited V-8 sequences to the portion of lef-2 indicated. FIG. 3D is the map of vEcoRIHybIFS recombinant virus containing the entire V-8 MluI (1.93 m.u.) to EspI (3.27 m.u.) fragment. The NaeI site in what was the 603 ORF has been destroyed via a four base pair deletion (asterisk denotes missing Nae I site).

FIGS. 4A–4D present the DNA sequence of AcMNPV L-1 (SEQ ID NO: 1) from the 327 ORF MluI site (nucleotide 2470) to the polh EspI site (nucleotide 4186) aligned with the corresponding sequence from the AcMNPV V-8 variant (SEQ ID NO:3). The V-8 sequence has a multitude of point mutations and four insertions as compared to the L-1 sequence. Identities are indicated by a vertical line. Sequence differences and insertions are in bold type. Startpoints of lef-2, the 603 ORF and polh are marked with asterisks (*). The natural termination codons of the L-1 lef-2 and 603 ORF are marked with pound signs. Crossover in vEcoRIHybI occurred in the dashed region between the two dollar signs at nucleotides 3003 and 3027. The premature stop codon generated by the insertion in the V-8 603 ORF is indicated by three consecutive carets. Sequence numbering in parentheses corresponds to that in O'Reilly et al. (1992) *Baculovirus Expression Vectors: A Laboratory Manual*, W.H. Freeman & Co., N.Y.

FIG. 5 presents the predicted amino acid sequences of AcMNPV L-1 and the V-8 lef-2 gene products (SEQ ID NO:2 and SEQ ID NO:4, respectively). Identities are designated by vertical lines. Differences are designated by bold type and a period between the differing amino acid residues. DNA sequence differences between the L-1 and the V-8 are responsible for six amino acid differences between the two lef-2 gene products. Amino acid differences occur at residues 14, 89, 101, 114, 153 and 190. The recombinant virus vEcoRIHybIFS is expected to contain all these lef-2 amino acid differences, but vEcoRIHybI is predicted to contain only the mutations at residues 153 and 190. The crossover event in vEcoRIHybI occurred in the DNA region that encodes the residues marked by a line of asterisks.

FIGS. 6A–6B present the nucleotide sequence of AcMNPV DNA in the region of the egt gene (SEQ ID NO:5). The codons for translation initiation (atg) and termination (taa) for the egt open reading frame are indicated over the sequence. The 1094 bp fragment deleted in the EGTDEL virus is underlined. The positions from which the oligonucleotide primers (EGTDEL1 and EGTDEL2) used for PCR amplification are shown.

FIG. 7 presents DNA sequences for AcMNPV E2 (SEQ ID NO:6), AcMNPV V-8 (SEQ ID NO:7) and V1000 (SEQ ID NO:8) virus strains beginning at the Esp3I site upstream of the polyhedrin gene and extending into the polyhedrin coding region. The sequences were from one strand using primer PVL Reverse, and nucleotides indicated as N were not identified.

DETAILED DESCRIPTION OF THE DISCLOSED EMBODIMENTS

Figure 1A:
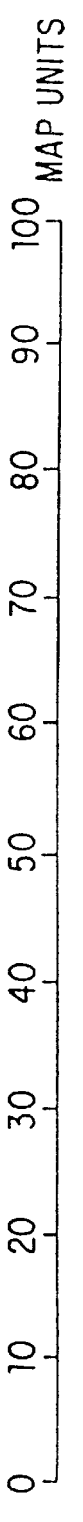
FIG. 1A provides a schematic representation of the AcMNPV genome showing the location of the egt gene. The AcMNPV genome is presented in map units and as EcoRI and HindIII restriction maps.

Because faster acting insect viruses are desirable as insect control agents, a study was undertaken to search for baculovirus strains with such improved killing properties. Toward this end, a minimally passaged (in insect larvae) AcMNPV virus stock was amplified, plated in culture to obtain clonal isolates, and these isolates were examined for restriction site polymorphisms and for increased virulence in insect larvae. A minimally passaged stock was used as the starting material for this survey, in part because serial passage in cell culture was known to lead to mutations and perhaps reductions in virulence in AcMNPV (see, e.g., Kumar and Miller (1987) *Virus Research* 7:335–349). Genotypic variants of AcMNPV were known (Lee and Miller (1978) *J. Virol.* 27:754–767). AcMNPV was the baculovirus for which a more virulent (i.e., faster killing) variant was sought because it is known to infect a relatively large number of insect pests of particular economic importance in agriculture.

The AcMNPV V-8 isolate was one of ten viral clones plaque purified on SF-21 cell monolayers inoculated with diluted hemolymph from *Heliothis virescens* larvae that had been orally infected with a minimal passage stock of the original Vail AcMNPV isolate (Vail et al., (1971) *Proc. IV Int. Collog. Insect Pathology*, College Park, Md. pp.297–304). All ten viral isolates, V-1 through V-10, were initially characterized by restriction endonuclease analysis with BamHI, BglII, EcoRI, HindIII, PstI, and XhoI and compared to AcMNPV L-1. The pattern of V-10 is identical to that of L-1. The profiles of V-1, V-2, V-3, V-6, V-7, V-8 and V-9 all lack the approximately 8.5 kb of HindIII-F fragment and instead contain two novel fragments of approximately 7.4 kb and 1.1 kb. Two isolates, V-4 and V-5, have a restriction pattern intermediate between the first two viral types (containing submolar quantities of the HindIII-F fragment and both the novel fragments of 7.4 kb and 1.1 kb). The presence of submolar fragments suggests that V-4 and V-5 are incompletely purified viral stocks, as all samples were plaque purified only once to preserve the virulence of the isolates. No differences in restriction profiles were detected between any of these ten clones and L-1 using BamHI, BglII, EcoRI, PstI, and XhoI digestion.

The V-8 isolate of AcMNPV was selected as representative of the predominant genotype of the ten isolates and was further characterized using *Spodoptera frugiperda* neonate bioassays. Data from representative bioassays evaluating oral infectivity ($LC_{50}$) and virulence ($LT_{50}$) are presented in Table 1. $LC_{50}$ is the amount of virus at which 50% of infected larvae are dead within ten days after infection. $LT_{50}$ is the time after infection when 50% of the infected larvae are dead when exposed to virus at $LC_{90}$ unless otherwise indicated hereinbelow. In *S. frugiperda* and *Trichoplusia ni* neonates, the $LC_{50}$s of the L-1 and V-8 AcMNPV strains are very similar, but the $LT_{50}$s are significantly different in *S. frugiperda* neonates. For AcMNPV strains E-2 and L-1, death from infection normally occurs at about the same time after infection while V-8 causes death more quickly post infection than the L-1 and E2 strains. There is variability in the actual time until death from experiment to experiment, but the results are consistent from experiment to experiment for comparisons of the percent difference in time until death in the V-8 versus L-1 or E-2 comparisons. The average $LT_{50}$ at $LC_{90}$ of the V-8 isolate in *S. frugiperda* neonates is consistently about 12% shorter than the average $LT_{50}$ of L-1.

Initial restriction analysis of AcMNPV V-8 versus AcMNPV L-1 with a battery of different restriction endonucleases (BamHI, BglII, EcoRI, HindIII, PstI, and XhoI) showed only the HindIII restriction polymorphism discussed above. The six restriction endonucleases used to characterize AcMNPV V-8 recognize a total of 95 sites in the AcMNPV genome, counting each EcoRI hr region (six short regions with highly repetitive DNA sequences and multiple EcoRI sites) as one site. Since each recognition site is a hexanucleotide, a total of 570 bp have been screened for mutations by restriction endonuclease analysis. The only difference found in this screen was a HindIII restriction polymorphism in lef-2 (a 0.18% mutation rate (1/570). The V-8 strain was subsequently shown to lack the EcoRV site which is located at about 90 bp upstream of the polyhedrin translation start site (see, e.g., FIG. 7).

Sequence analysis of 1.72 kb in the region surrounding the HindIII polymorphism revealed numerous nucleotide differences between L-1 and V-8 sequences in and around lef-2, the 603 ORF, and the polyhedrin gene (polh) (1.93 map units (m.u.) to 3.27 m.u.) (FIG. 2). There are 73 nucleotide changes in the 1.72 kb sequenced region. The HindIII restriction polymorphism in V-8 is due to a C to T mutation at nucleotide 3243. Both the MluI site (3389) in the 603 ORF and the EcoRV site (4001) between the polyhedrin gene and the 603 ORF were destroyed by single nucleotide changes (FIGS. 4A–4D and 5). Several nucleotide substitutions in this region result in amino acid sequence changes in the predicted polypeptide products of lef-2, while insertions and substitutions substantially alter the 603 ORF. The six predicted amino acid changes in lef-2 are shown in FIG. 5. A 26 bp insert in the 603 ORF creates a stop codon within the open reading frame of the 603 ORF and is predicted to cause premature termination during 603 ORF translation. No sequence differences were discovered in the 327 ORF as far upstream as the MluI site. Only three DNA sequence differences between V-8 and L-1 were discovered in polh. These are third base pair changes which do not change the encoded amino acids. The region about 90 bp upstream of the polyhedrin translation start site of polh was generally unchanged, although the EcoRV site present in L-1 is absent in V-8.

Therefore, based on sequence and restriction analysis, this region of V-8 contains an unusually high density of mutations using L-1 as a wild-type comparison. Without wishing to be bound by any particular theory, it is postulated that AcMNPV V-8 arose by recombination between AcMNPV and a virus relatively distantly related to AcMNPV. Furthermore, considering the mutation density of V-8 in this region, the differences at nucleotides 2703 and 4194 of V-8 (FIGS. 4A–4D) may be the limits of the recombination, as no sequence differences were found as far downstream of the BamHI site in polh and as far upstream as the 327 ORF MluI site (beginning at nucleotide 1 in SEQ ID NO:3) at nucleotide 2469 FIGS. 4A–4D and FIG. 7. Most of the mutations are concentrated in the 603 ORF and, to a lesser extent, in lef-2. Furthermore, complete V-8 vs. L-1 sequence analysis of the relatively distant 504 ORF (a phosphatase gene located between 0.0 m.u. and 0.4 m.u.) revealed no differences between L-1 and V-8.

The *H. virescens* colony at the American Cyanamid Agricultural Research Center, Princeton, N.J., was derived from a field isolate (Stoneville, Miss.) in 1966, and has been maintained since 1966. Air, water and diet are not thoroughly sterilized before coming in contact with *H. virescens*. It has been discovered that there are sporadic viral outbreaks in this colony. Virus, termed V1000, has been isolated from this colony, partial genomic DNA sequence has been determined and various properties of the virus have been characterized. The V1000 Nuclear Polyhedrosis Virus appears to be most closely related to *Rachiplusia ou* Nuclear Polyhedrosis Virus (RoNPV) based on restriction endonuclease analysis.

Based on a sequence comparison of V-8 and V1000 polyhedrin regions, but without wishing to be bound by any particular theory, it is postulated that AcMNPV strain V-8 is a recombinant between AcMNPV and the V1000 virus. A comparison of sequence between AcMNPV E-2 (ATCC VR-1344, American Type Culture Collection, 12301 Parklawn Drive, Rockville, Md.), V1000 and AcMNPV V-8 is presented in FIG. 7. The last sequence difference between the AcMNPV V-8 and E-2 strains occurs at the twentieth codon of the polyhedrin coding sequence.

Two recombinant viruses, vEcoRIhybI and vEcoRIHybIFS, were constructed by allelic replacement (see Example 3 and FIG. 2) to determine if the reduced $LT_{50}$ of AcMNPV V-8 was correlated with the sequence differences observed in the lef-2 region. Sequence analysis established which V-8 characteristic sequence differences these recombinants possessed following allelic recombination. Both recombinants had recombined downstream of the KpnI site in polh as evidenced by their occlusion positive phenotype. The parent virus vSynVI⁻gal lacks polh sequences upstream of the KpnI site. The virus vEcoRIHybIFS contained the entire 1.72 kb MluI to EspI (1.93–3.27 m.u.) fragment with a four bp deletion at the NaeI site in what was the 603 ORF. The deletion in the V-8 603 ORF was intended to destroy the function of the product of the 603 ORF, but subsequent sequence analysis revealed that the V-8 603 ORF was already disrupted. Thus, this deletion is expected to have no additional effect on viral infectivity and virulence. Crossover during the allelic replacement event generating VEcoRIHybI occurred at some point between nucleotides 3003 and 3027 of AcMNPV sequence in FIGS. 4A–4D (between nucleotides 535 and 559 of SEQ ID NO:3; FIGS. 4A–4D and 6) and before the KpnI site within the polyhedrin gene. Thus, the lef-2 gene product of VEcoRIHybI is predicted to be a hybrid containing L-1-like amino acid residues upstream of the crossover and V-8-like residues downstream of the crossover FIGS. 4A–4D and 6A–6B.

Bioassays to determine infectivity and virulence of the viruses L-1, V-8, VEcoRIHybI, and VEcoRIHybIFS were performed on *Spodoptera frugiperda* neonates. Both $LC_{50}$s and $LT_{50}$s were computed using probit analysis (Daum (1970) *Bulletin of the Entomological Society of America* 16:10–15) for each virus (Table 1). The $LC_{50}$s of all four viruses were statistically equivalent. As previously noted, V-8 has a 12.4% shorter $LT_{50}$ at $LC_{90}$ than L-1, reflecting increased virulence. The differences between the $LT_{50}$s at $L_{90}$ of V-8, vEcoRIHybI and vEcoRIHybIFS are not statistically significant. However, the differences between the $LT_{50}$s at $LC_{90}$ of L-1 and each of the three viruses containing V-8 DNA are statistically significant; V-8 and the two hybrid viruses each had a significantly shorter $LT_{50}$ than L-1. Hybrid virus vEcoRIHybI contains only a small region of the V-8 sequences from the middle of lef-2 to the 5' end of polh but possesses the increased virulence characteristic of V-8. The fact that the lef-2 gene product of vEcoRIHybI has an L-1-like amino-terminus and a V-8 carboxy-terminus but still retains the V-8 virulence phenotype indicates that the increased virulence (decreased $LT_{50}$) of V-8 is due either to one or both of the lef-2 carboxy-terminal amino acid differences or to the absence of a functional 603 ORF gene product, or some combination thereof. Alternatively, the V-8 faster killing (increased virulence) phenotype may be due to cis-acting sequence effects.

Whether the two carboxy-terminal lef-2 amino acid differences, the non-functional 603 ORF or a combination of these differences is responsible for the increased virulence of V-8 remains to be determined. Gearing and Possee (1990) *J. Gen. Virol.* 71:251–262 determined that the 603 ORF is not essential for production of budded virus in cell culture, production of polyhedra, or the infectivity ($LC_{50}$) of AcMNPV. However, Gearing and Possee presented no data relevant to the virulence as measured by $LT_{50}$ of their 603 ORF deletion mutant, so it is not known what effects the destruction of the 603 ORF had on the virulence of their mutant. Passarelli and Miller (1993) *J. Virol.* 67:2149–2158 reported that lef-2 and its 630 amino acid expression product is required for late and very late gene expression in transient expression assays. Without wishing to be bound by any particular theory, it is postulated that one or both of the V-8 lef-2 and 603 ORF alleles affect the rate of virus replication and therefore the virulence of the virus. It is possible that the faster killing by the V-8 strain is due to a cis or trans effect. The phenotype is believed to be carried within the region between nucleotides 3027 and 4231 in the V-8 sequence shown in FIGS. 4A–4D.

TABLE 1A

Bioassays of the infectivity of AcMNPV variants in *S. frugiperda* neonates.

| Virus | $LC_{50}$ | Fiducial Limits Upper | Fiducial Limits Lower | Slope |
|---|---|---|---|---|
| L-1 | $4.6 \times 10^5$ | $6.8 \times 10^5$ | $3.0 \times 10^5$ | 0.81 |
| V-8 | $3.0 \times 10^5$ | $4.3 \times 10^5$ | $2.0 \times 10^5$ | 0.97 |
| vEcoRIHybI | $5.5 \times 10^5$ | $1.3 \times 10^6$ | $1.9 \times 10^5$ | 0.96 |
| vEcoRIHybIFS | $2.1 \times 10^5$ | $2.9 \times 10^5$ | $1.4 \times 10^5$ | 1.06 |

$LC_{50}$s (#PIBs/ml diet; polyherin inclusion bodies/ml) for L-1, V-8, vEcoRIHybI, and vEcoRIHybIFs were statistically equivalent.

TABLE 1B

Bioassays of the Virulence of AcMNPV Variants in *S. frugiperda* neonates

| Virus | $LT_{50}$ | Fiducial Limits Upper | Fiducial Limits Lower | Slope |
|---|---|---|---|---|
| L-1 | 129.4 | 134.1 | 125.7 | 12.35 |
| V-8 | 113.3 | 116.1 | 110.8 | 14.39 |
| vEcoRIHybI | 116.9 | 120.7 | 113.7 | 10.64 |
| vEcoRIHybIFS | 115.0 | 117.9 | 112.3 | 13.50 |

(B) The $LT_{50}$s (in hours) at $LC_{90}$ of V-8, vEcoRIHybI, and vEcoRIHybIFS were 10–12% faster than the $LT_{50}$ of L-1 at $LC_{90}$; this difference is statistically significant, as evidenced by the upper and lower fiducial limits.

The AcMNPV V-8 was genetically modified to inactivate the egt gene (egt encodes ecdysteroid glycosyl transferase) following substantially the same procedure as described in U.S. Pat. No. 5,180,581. Then the $LT_{50}$ values were determined using *S. frugiperda* neonates for AcMNPV L-1, the egt-deficient derivative of L-1 (vEGTDEL), AcMNPV V-8 and the V-8 derivative in which the egt gene was inactivated (V8vEGTDEL). The results are shown in Tables 2 and 3. Clearly, AcMNPV V-8 killed faster than L-1, and V8vEGTDEL killed even faster than the AcMNPV V-8.

*S. frugiperda* neonate bioassays

| Virus | V8 | V8vEGTDEL isolate 1 | L1 | vEGTDEL | V8vEGTDEL isolate2 |
|---|---|---|---|---|---|
| A. Dose: $2 \times 10^7$ PIB/ml (100% mortality) | | | | | |
| Upper limit | 90 | 75.7 | 106 | 86.8 | 77 |
| LT50 | 84 | 70.6 | 103.6 | 81.5 | 72 |
| Lower limit | 84 | 66 | 101 | 76.5 | 68 |
| B. Dose: $5 \times 10^6$ PIB/ml (92% to 100% mortality) | | | | | |
| Upper limit | 91.8 | 83 | 109 | 101 | 85.5 |
| LT50 | 86.4 | 76.5 | 105 | 93 | 79 |
| Lower limit | 81 | 70.6 | 102 | 85.6 | 73 |

TABLE 3

Bioassays of $LT_{50}$s V8, L-1 and egt deletions in *S. frugiperda* neonates

| Virus | Upper Limit | LT50 | Lower Limit | % kill |
|---|---|---|---|---|
| A. | | | | |
| V8vEGTDEL | 81.6 | 75.4 | 69.8 | 96 |
| V8 | 99.6 | 95 | 91 | 90 |
| B. | | | | |
| L-1 | 106 | 102 | 98 | 90 |
| vEGTDEL | 89.7 | 84.2 | 78.9 | 96 |

In diet overlay bioassays using second instar *H. virescens* larvae, $LT_{50}$ values for V8vEGTDEL were lower than for the corresponding V-8 virus, and V-8 had lower $LT_{50}$ values than the L-1 strain. The vEGTDEL and V-8 had similar $LT_{50}$ values, and V8vEGTDEL had lower $LT_{50}$ than vEGTDEL (L-1). Using diet overlay tests with second instar *Helicoverpa zea* larvae, V8vEGTDEL exhibited significantly faster killing than AcMNPV E2. In insect larval tests, V8vEGTDEL appeared to kill infected insects faster than the AcMNPV L-1 egt-deletion strain (vEGTDEL). $LC_{50}$ values calculated on PIBs/16 cm² arena in diet overlay bioassays for AcMNPV wild-type strains (as E2 or L-1) were $1 \times 10^5$ to $1 \times 10^6$ for *S. frugiperda* and *H. zea*; $1 \times 10^3$ to $1 \times 10^4$ for *S. eridania*; and $1 \times 10^1$ to $1 \times 10^2$ for *T. ni, S. exigua* and *H. virescens*.

Thus, preferred viruses for insect control carry both a genetic region conferring the increased virulence phenotype and a genetic modification inactivating the gene encoding ecdysteroid glycosyl transferase. Preferred regions carrying the increased virulence phenotype are those from region of the lef-2 and ORF 603 region of the RoNPV genome. Functional equivalents of this regions from other baculoviruses can be readily identified, isolated and manipulated using the teachings of the present disclosure and technology well known to the art.

Lepidopteran insects undergo a well characterized sequence of events during development from egg to adult insect (see *Comprehensive Insect Physiology, Biochemistry and Pharmacology*, Vols. 7 and 8, Kerkut and Gilbert (eds.), Pergamon Press, Oxford, 1984 for detailed reviews). After hatching, the insect larva enters a period of extensive feeding during which time it will molt several times to allow continued growth. Stages between successive molts are known as instars. At the end of the larval growth period, the larva pupates and finally emerges as an adult insect. The processes of molting and pupation (collectively termed ecdysis) are regulated by the concerted actions of several different groups of hormones. The initial stimulus is the release of prothoracicotropic hormone (PTTH) by certain brain cells. This stimulates the prothoracic glands to produce and secrete ecdysteroids, often referred to as insect molting hormones. In the presence of juvenile hormone, a larval molt will ensue, while in the absence of juvenile hormone, the larvae will pupate. Eclosion hormone is also important in mediating several behavioral changes associated with ecdysis.

AcMNPV, which is used as a model system for much baculovirus research, interferes with the process of insect development. Insect larvae infected with AcMNPV are no longer able to molt or pupate because AcMNPV directs the synthesis of an enzyme, known as ecdysteroid UDP-glycosyltransferase (EGT), which specifically inactivates the insect ecdysteroids by conjugating them to galactose in vivo (O'Reilly et al. (1991) Insect Biochem. Molec. Biol. 22:313–320) or glucose in vitro (O'Reilly et al. Science 245:1110–1112). Other baculoviruses carry egt genes as well.

The AcMNPV gene encoding EGT extends from 8.4 to 9.6 map units on the AcMNPV genome (FIGS. 1A–1C and 2). FIG. 2 shows the restriction map of the egt region of the genome. The nucleotide sequence of the AcMNPV (strain L1) egt gene and the deduced amino acid sequence of 506 amino acids are shown in SEQ ID NO:1 and 2, respectively. The coding sequence of egt extends from nucleotide 149 to about nucleotide 1670.

In a preferred embodiment of the present invention, the egt gene of the AcMNPV V-8 strain is inactivated by replacing a portion of the egt gene with a bacterial sequence encoding β-galactosidase. This recombinant baculovirus is designated V8vEGTDEL herein. In a second preferred embodiment, part of the egt gene of the V8 strain AcMNPV is deleted without replacement, for example, by deleting an EcoRI/XbaI segment from within the egt coding sequence (See FIGS. 6A–6B; U.S. Pat. No. 5,180,581; Example 7 hereinbelow). An alternate mechanism for the inactivation of the insect virus egt gene is the insertion of a gene encoding an insect hormone affecting ecdysis, an enzyme which inactivates an insect hormone affecting ecdysis, which gene is expressible in an insect cell infected with said insect virus or an insect-specific toxin gene.

Using the AcMNPV egt gene as a probe, an egt gene has been identified in the baculovirus *Orgyia pseudotsugata* nuclear polyhedrosis virus (OpMNPV). It will be recognized by those skilled in the art with the benefit of this disclosure that the egt gene of any baculovirus can be characterized and isolated in a similar manner as AcMNPV (see, e.g., U.S. Pat. No. 5,180,581, incorporated by reference herein in its entirety). egt genes with at least 70% nucleotide sequence homology to the egt coding sequence in FIGS. 6A–6B from nucleotides 149 to 1666 (and in SEQ ID NO:1, from nucleotide 149 to 1666) are considered equivalent to said sequence, provided those homologous genes encode an enzyme which is an ecdysteroid UDP-glycosyl transferase, and their identification, isolation and manipulation will be readily achieved by the skilled worker using the sequences and assay information provided, taken together with what is well known in the art.

Functional equivalents of the egt gene are those which also catalyze the inactivation of ecdysteroids such as ecdysone by transferring a glucose or galactose moiety from UDP-glucose to the ecdysteroid(s). Those functional equivalents of egt may be identified using the assay methods described herein.

By inhibiting molting and pupation via the effects of ecdysteroid glycosyl transferase, wt AcMNPV infection can actually prolong larval feeding time. Baculoviruses which lack a functional egt gene do not prolong larval feeding time. Larvae infected with egt-deficient baculoviruses may pupate, and they succumb to the viral infection even more rapidly than larvae infected with the corresponding wt virus. The more rapid killing by a baculovirus lacking a functional egt gene is most dramatically seen when newly hatched first instar larvae are infected with wt AcMNPV and with vEGTZ. Larvae infected with vEGTZ succumb to the viral infection 3 to 4 days sooner than larvae infected with wt AcMNPV. Therefore, baculoviruses lacking a functional egt gene are considerably more effective as insect control agents than wild-type baculoviruses. It will be apparent to those skilled in the art with the benefit of this disclosure that the egt gene can be rendered nonfunctional in any baculovirus by any means known to the art.

Although the length of time progeny virus can accumulate in larvae infected with baculoviruses lacking a functional egt gene is somewhat truncated and the infected insect displays reduced growth, there is substantial production of progeny virus. The amount of virus obtained per larva following vEGTZ infection of late instar larvae is about 15 to 50% that obtained with wt virus. This is sufficient to allow cost-effective preparation of large quantities of virus particles.

In another embodiment of the present invention, an insect virus lacking a functional egt gene is modified by genetic engineering techniques so that its effectiveness as a biological control agent is further enhanced by incorporating a second gene whose product affects insect development.

The gene encoding PTTH (a peptide hormone) can be inserted into the viral genome with the egt gene inactivated and PTTH can be expressed at levels sufficiently high to affect ecdysis. Insect larvae infected with such a virus experience extreme disruption in the hormonal control of development. These insects become sick rapidly resulting in severely compromised growth and development, reduced feeding, and earlier death. PTTH sequences are described in Kawakami et al. (1990) Science 247:1333).

It is important to note that, while all of the above genes could be added to wild-type virus genome using disclosure provided herein and/or in U.S. Pat. No. 5,180,581 and techniques well known to the art, they would not be expected to significantly affect insect behavior in the wild-type virus because expression of the egt gene by wild-type virus inactivates the ecdysteroid molting hormones and ecdysis is prevented, regardless of the production of other hormones. Thus, successful strategies involving the generation of viruses designed to interfere with insect ecdysis depend upon prior inactivation of the egt gene.

It will be understood by those skilled in the art that mutant organisms lacking an intact egt gene or incapable of expressing a functional egt product and those which are further genetically modified so as to express another hormone-modifying enzyme or a peptide developmental hormone are included as insect control agents of the present invention.

An isolated and purified insect virus is one which has been cloned through plaque purification in tissue culture, for example, or otherwise prepared from a single viral genotype. A recombinant insect virus, as used herein, is one which has at least one portion of its genotype derived from a heterologous insect virus, i.e., an insect virus of different taxonomic viral species. A recombinant insect virus may be generated by co-infection of one insect cell or insect with more than one viral species, or it may be the result of introducing insect virus genomic DNA and a heterologous insect DNA virus segment into the same insect or insect cell, with the result that a portion of the heterologous DNA becomes incorporated in the insect virus genome by recombination process. It is understood in the art that such a recombinant virus can be recognized via restriction endonuclease analysis, DNA sequencing at least a portion of the putative recombinant genome or via a change in phenotype. As specifically exemplified herein, recombinant insect viruses are recognized by their increased virulence phenotype (lower $LT_{50}$) in at least one target insect as compared with the parental insect virus. A recombinant insect virus phenotype with the faster killing phenotype can be further genetically modified and further improved as an insect control agent by inactivating an ecdysteroid modifying enzyme, for example.

As used herein, an insecticidal composition has at least one active ingredient which has an adverse affect on insect pests, preferably which kills said pests. The present invention is the use of a recombinant insect virus which has been isolated or which has been genetically engineered to kill at least one insect pest faster than the corresponding wild-type comparison using a segment of heterologous insect virus DNA. A heterologous insect virus DNA segment is one which is not normally associated with the genome of the parent of the recombinant virus. As specifically exemplified herein, a portion of a baculovirus genome has been isolated and identified and shown to confer a phenotype of faster insect killing (as measured using the $LT_{50}$ assay) when inserted into the AcMNPV L-1 genome, with *Spodoptera frugiperda* as the target insect. When an Egt-deficient derivative of that recombinant insect virus is used, feeding by insects is reduced in response to the insect egt-deficient recombinant virus, normal insect ecdysis is disrupted and death of the insect is further accelerated relative to the isogenic wild-type strain (i.e., with functional egt). A recombinant virus of this invention can also be an insect virus genetically engineered to inactivate a gene encoding an ecdysteroid modifying enzyme or one which is further engineered to express a heterologous gene encoding a protein which affects insect development, so as to minimize the time of insect feeding or to cause more rapid killing after virus infection.

It will be understood by those skilled in the art that the insect pests can be exposed to the viruses of the present invention by conventional methods including ingestion, inhalation or direct contact of the insect control agent.

A primary use of the recombinant and/or genetically engineered baculoviruses of the present invention will be as active ingredients of agricultural compositions for applying to plants to effect the biological control of insect pests of plants. Many variations of preparing such agriculturally suitable compositions for insect control are known in the art. The insecticidal compositions of this invention are typically administered at dosages in the range of $2.4 \times 10^8$ to $2.4 \times 10^{12}$ PIBs/hectare of recombinant insect virus.

Insecticidal compositions suitable for applications to plants to control insect pests comprise an agriculturally suitable carrier and an insect control agent, i.e., an insect virus, preferably a baculovirus. Conventional formulation technology known to persons skilled in the art is used to prepare the compositions of this invention. The compositions can be in the form of wettable powders, dispersible granular formulations, granules, suspensions, emulsions, solutions for aerosols, baits and other conventional insecticide preparations. Wetting agents, coating agents, agents to promote physical flexibility, UV protectants, dispersants and sticking agents are desirable additives in at least some formulations. The compositions will frequently include an inactive carrier, which can be a liquid such as water, alcohol, hydrocarbons or other organic solvents, or a mineral, animal or vegetable oil, or a powder such as talc, clay, silicate or kieselguhr. A nutrient such as sugar may be added to increase feeding behavior and/or to attract insects. Flow agents, for example, clay-based flow agents, may be added to minimize caking of the wettable powders or other dry preparations during storage. Application of an insecticidal composition of this invention can protect plants from insect pests by reducing feeding by and killing of susceptible insects.

The skilled artisan knows how to choose an insect virus which is suitable for the control of a particular insect pest. The concentration of the insect control agent that will be required to produce insecticidally effective agricultural compositions for plant protection will depend on the type of crop, target insect, virus genotype used and the formulation of the composition. Insecticidal compositions may be formulated, for example, as wettable powders, with about 10% (w/w) polyhedrin inclusion bodies. The insecticidally effective concentration of the insect control agent within the composition can readily be determined experimentally by a person of ordinary skill in the art.

Agricultural compositions must be suitable for agricultural use and dispersal in fields. Generally, components of the composition must be non-phytotoxic and not detrimental to the integrity of the occluded virus. Foliar applications must not damage or injure plant leaves. In addition to appropriate solid or, more preferably, liquid carriers, agricultural compositions may include sticking and adhesive agents, emulsifying and wetting agents, but no components which deter insect feeding or any viral functions. It is desirable to add components which protect the insect control agent from UV inactivation. Agricultural compositions for insect pest control may also include agents which stimulate insect feeding.

Reviews describing methods of application of biological insect control agents and agricultural application are available. See, for example, Couch and Ignoffo (1981) in *Microbial Control of Pests and Plant Disease* 1970–1980, Burges (ed.), chapter 34, pp. 621–634; Corke and Rishbeth, ibid, chapter 39, pp. 717–732; Brockwell (1980) in *Methods for Evaluating Nitrogen Fixation*, Bergersen (ed.) pp. 417–488; Burton (1982) in *Biological Nitrogen Fixation Technology for Tropical Agriculture*, Graham and Harris (eds.) pp. 105–114; and Roughley (1982) ibid, pp. 115–127; *The Biology of Baculoviruses*, Vol. II, supra.

Field trials in which AcMNPV E-2, V8vEGTDEL and a commercial *Bacillus thuringiensis* subsp. kurstaki insecticide (DIPEL 2X, Abbott Laboratories, Chicago, Ill.) were carried out during the fall growing season in Arizona. Although the pest infestation was relatively light, results from this study indicated that V8vEGTDEL was efficacious against *T. ni* in young lettuce (Table 4). Following the fourth application of treatments (on ca. 5-day intervals), V8vEGTDEL at $1 \times 10^{11}$ and $1 \times 10^{12}$ PIBs/A provided better control of *T. ni* than similar doses of AcMNPV-E2 "wild-type". Additionally, V8vEGTDEL at $1 \times 10^{11}$ and $1 \times 10^{12}$ PIBs/A provided control of the *T. ni* infestation at levels equal to that provided by DIPEL 2X at 1 lb/A. Based on data collected after only three applications, however, DIPEL 2X provided better pest control than either baculovirus.

After completion of data collection, the test site (as well as 10-ft wide perimeter) was sprayed with an aqueous dilution of 1% (v/v) bleach. The treated crop, as well as a 10-ft wide perimeter, was then destroyed by using tractor-mounted tillage equipment. About 3 weeks later, soil samples were collected from several sites located within 100 ft of the test site. No V8vEGTDEL virus were detected in soil surrounding the test site, and no additional action was taken.

TABLE 4

Efficacy of selected baculovirus treatments against *Trichoplusia ni* in lettuce

| Treatment[1] | Dose/A[2] | Mean # larvae/10 plants at 3DA3T | Mean # larvae/10 plants at 5DA4T |
| --- | --- | --- | --- |
| V8vEGTDEL | $1 \times 10^{10}$ PIBs | 15 a b[3] | 20 a |
| | $1 \times 10^{11}$ PIBs | 20 a | 2 c |
| | $1 \times 10^{12}$ PIBS | 12 b | 7 b c |

TABLE 4-continued

Efficacy of selected baculovirus treatments against
*Trichoplusia ni* in lettuce

| Treatment[1] | Dose/A[2] | Mean # larvae/10 plants at 3DA3T | Mean # larvae/10 plants at 5DA4T |
|---|---|---|---|
| AcMNPV E2 | $1 \times 10^{10}$ PIBs | 10 b | 18 a |
|  | $1 \times 10^{11}$ PIBs | 18 a | 20 a |
|  | $1 \times 10^{12}$ PIBs | 12 b | 10 b |
| DIPEL 2X | 1 lb form | 0 c | 7 b c |
| Untreated | — | 20 a | 18 a |

[1]Baculovirus compositions were formulated as water-soluble wettable powders ($1 \times 10^{11}$ PIBs/10 gm).
[2]Baculovirus compositions were applied at $1 \times 10^{E9}, 1 \times 10^{11}$, and $1 \times 10^{13}$ PIBs/A on day 15, however, due to poor mixing and spray characteristics of the $1 \times 10^{13}$ dose, both baculovirus were applied at $1 \times 10^{10}$, $1 \times 10^{11}$ and $1 \times 10^{12}$ PIBs/A in all subsequent applications at days 5, 10 and 15. DIPEL 2X was also applied on days 1, 5, 10 and 15.
[3]Means within columns followed by the same letter are not significantly different (DMRT, P = 0.05).

In a second fall field trial, the efficacy of V8vEGTDEL, AcMNPV E2 and a commercial *B. thuringiensis* subsp. kurstaki insecticide (DIPEL 2X, Abbott Laboratories, Chicago, Ill.) against the cabbage looper in New Jersey. Viral insecticidal compositions were formulated as wettable powders.

Due to the light pest infestation in this study, differences among treatments in control of *T. ni* larvae were very slight (and generally not statistically significant). However all treatments had significantly fewer live larvae and less plant defoliation than untreated cabbage (Table 5). At 7 days after last application of treatments, untreated plots averaged 18% defoliation whereas cabbage treated with V8vEGTDEL or AcNPV-E2 "wild type" (rates of $1 \times 10^9$, $1 \times 10^{11}$, and $1 \times 10^{12}$ PIBs/A) averaged 8–10% defoliation and DIPEL-treated (1 lb/A) cabbage averaged 4% defoliation. At 12 days after last application, untreated plots had a mean of 6.5 live larvae/10 plants whereas baculovirus-($1 \times 10^{11}$ and $1 \times 10^{12}$ PIBs/A) and DIPEL-treated plots averaged <2 larvae/10 plants.

After data collection was complete, the test site (as well as 10-ft wide perimeter) was sprayed with an aqueous dilution of 1% (v/v) bleach. The treated crop, as well as a 10-ft wide perimeter, was then destroyed by using tractor-mounted cultivation equipment. About five months after the bleach treatment, soil samples were again collected from several sites located within 100 ft of the test site. Also on this date, the test site was treated with AcMNPV-E2 "wild-type" at a rate of $1 \times 10^{12}$ PIBs/A. No V8vEGTDEL was detected in these later soil samples.

TABLE 5

Efficacy of selected baculovirus treatments against
*Trichoplusia ni* in cabbage

| Treatment[1] | Dose/A[2] | Mean # larvae/10 plants at 7DA3T | Mean # larvae/10 plants at 12DA3T |
|---|---|---|---|
| V8vEGTDEL | $1 \times 10^9$ PIBs | 10 b[3] | 2.0 b |
|  | $1 \times 10^{11}$ PIBs | 11 b | 1.2 b c |
|  | $1 \times 10^{12}$ PIBs | 7 b c | 1.7 b c |
| AcMNPV E2 | $1 \times 10^9$ PIBs | 8 b c | 2.0 b |
|  | $1 \times 10^{10}$ PIBs | 8 b c | 0.8 b c |
|  | $1 \times 10^{12}$ PIBs | 11 b | 0.8 b c |
| DIPEL 2X | 1 lb form. | 4 c | 0.2 c |
| Untreated | — | 8 a | 6.5 a |

[1]Both types of baculoviruses were formulated as water-soluble wettable powders (1E11 PIBs/10 gm of WP).
[2]"EGT-deleted" and "Wild-type" (at $1 \times 10^9$ and $1 \times 10^{11}$ PIBs/A) and DIPEL 2X were applied three times. Due to severe clogging of nozzles, the planned baculovirus does of $1 \times 10^{13}$ PIBs/A, so no baculovirus "high dose" was applied at the first application and V8vEGTDEL and AcMNPV E2 at $1 \times 10^{12}$ PIB/A were applied and were subsequently applied only twice (5 and 10 days later).
[3]Means within columns followed by the same letter are not significantly different (DMRT, P = 0.05).

A third field trial for efficacy of V8vEGTDEL, AcMNPV E2 and a commercially available *B. thuringiensis* subsp. awaizai insecticide (Xentari, Abbott Laboratories, Chicago, Ill.) for control of *T. ni* in lettuce was carried out in spring in Florida.

The data are summarized in Table 6. V8vEGTDEL provided significantly faster control of *T. ni* than AcMNPV V8. Five days after treatment with V8vEGTDEL ($1 \times 10^{12}$ PIBs/A) caused 100% larval mortality whereas V8 at the same dose caused only 29% larval mortality (up to 97% mortality by day 7). Also, V8vEGTDEL ($1 \times 10^{11}$ PIBs/A) exhibited larval control at a rate equal to that of V8 at $1 \times 10^{12}$ PIBs/A.

The commercial Bt product XENTARI (1 lb form./A), provided 76% larval control by day 4 vs. only 40% larval control from V8vEGTDEL ($1 \times 10^{12}$ PIBs/A). However, by day 5, V8vEGTDEL ($1 \times 10^{12}$ PIBs/A) and XENTARI (1 lb/A) exhibited 100% and 89% larval mortality, respectively.

TABLE 6

Efficacy of field applications of V8vEGTDEL and AcMNPV V8 ("wild-type") against *Trichoplusia ni* in lettuce

| Treatment[1] | Dose per acre | Mean % larval mortality[2] | | | |
|---|---|---|---|---|---|
|  |  | Day 4 | Day 5 | Day 6 | Day 7 |
| V8vEGTDEL | $1 \times 10^{11}$ PIBs | 0 | 35 | 88 | 100 |
| V8vEGTDEL | $1 \times 10^{12}$ PIBs | 40 | 100 | — | — |
| AcMNPV V-8 | $1 \times 10^{12}$ PIBs | 4 | 29 | 68 | 97 |
| XENTARI | 1 lb | 76 | 89 | 92 | 95 |

[1]Baculovirus compositions were formulated as wettable powder.
[2]Treatments were applied to six true-leaf lettuce (4 plots/treatment, RCT design). About 3 hrs. after application, leaves were harvested from field-plots, individually placed into petri dishes containing water-moistened filter paper, and then infested with three-day-old *T. ni* larvae (ca. 10 larvae/leaf). Two days later, larvae were placed in CD-International trays containing untreated Stoneville artificial diet (1 larva/diet-well), and percent mortality was rated on each of several days post-treatment.

The examples provided herein use many techniques well known and accessible to those skilled in the arts of molecular biology, in the manipulation of recombinant DNA in plant tissue and in the culture and regeneration of transgenic plants. Enzymes are obtained from commercial sources and are used according to the vendors' recommendations or other variations known to the art. Reagents, buffers and culture conditions are also known to the art. References providing standard molecular biological procedures include Sambrook et al. (1989) *Molecular Cloning*, second edition, Cold Spring Harbor Laboratory, Plainview, N.Y.; R. Wu (ed.) (1993) *Methods in Enzymology* 218; Wu et al. (eds.) *Methods in Enzymology* 100, 101; Glover (ed.) (1985) *DNA Cloning*, Vols. I and II, IRL Press, Oxford, UK; and Hames and Higgins (eds.) (1985) *Nucleic Acid Hybridization*, IRL Press, Oxford, UK. Abbreviations and nomenclature, where employed, are deemed standard in the field and are commonly used in professional journal such as those cited herein. All references cited in the present application are expressly incorporated by reference herein.

This invention is illustrated by the following examples, which are not to be construed in any way as imposing limitations on the scope thereof. It is understood that resort may be had to various other embodiments, modifications, and equivalents thereof which, after reading the description herein, may suggest themselves to those skilled in the art without departing from the spirit of the present invention and/or the scope of the appended claims.

THE EXAMPLES

Example 1
Isolation of AcMNPV V-8

A minimally passaged AcMNPV stock from the original AcMNPV isolated by Pat Vail (Vail et al. (1971) Proc. IV Int. Colloq. Insect Pathology, College Park, Md. pp. 297–304) was amplified in *Heliothis virescens* larvae from the *H. virescens* colony at American Cyanamid, Princeton, N.J. The *H. virescens* are reared on a soybean-wheat germ agar-ased diet at 28 C. under constant fluorescent light. Virus was then further amplified in *H. virescens* larvae. Ten viral clones were plaque-purified from diluted hemolymph from the latter infected *H. virescens* larvae. Methods for plaque assay, plaque purification, virus amplification and viral DNA preparation are described in O'Reilly et al. (1992) *Baculovirus Expression Vectors; A Laboratory Manual*, W.H. Freeman & Co., New York, N.Y. Unless otherwise indicated, viruses were propagated in the IPLB-SF-21 cell line (SF-21) (Vaughn et al., 1977) In Vitro 13:213–217) using TC100 medium (Gibco BRL, Gaithersburg, Md.) supplemented with 0.26% tryptose broth and 10% fetal bovine serum (Intergen, Purchase, N.Y.). SF-21 cells are commercially available (e.g., Invitrogen Corporation, San Diego, Calif.). DNA was prepared from each isolate and characterized by restriction endonuclease analysis in parallel with DNA prepared from the L-1 strain of AcMNPV, which is described in Lee and Miller (1978) *J. Virol.* 27:754.

Example 2
Analysis of the AcMNPV lef-2 and 603 ORF Region

Molecular biology techniques were used as previously described (Maniatis et al., 1989). Plasmid pRI-I contains the 7.33 kb AcMNPV L-1 EcoRI-I fragment cloned in the EcoRI site of pBR322. Plasmid pEcoRI-IV8 contains the V-8 EcoRI-I fragment in the EcoRI site of Bluescript KS+ (Stratagene, La Jolla, Calif.). Plasmid pEcoRIHybI was constructed by replacing the 1.72 kb MluI to EspI fragment (1.93–3.27 m.u.) in the L-1 EcoRI-I fragment with the corresponding fragment from V-8. The hybrid EcoRI-I fragment was then recloned into a pUC19 vector, producing pUC19HybI, a plasmid with a unique NaeI site in the 603 ORF. A plasmid with a frameshift mutation at this NaeI site, pUC19HybIFS, was produced by digesting pUC19HybI with NgoAIV (an isoschizomer of NaeI which produces cohesive ends), blunt-ending the overhanging ends with mung bean nuclease, and relegating the blunt ends to produce a four base pair deletion that destroys the NaeI site and disrupts the 603 ORF reading frame. This frameshift, which was confirmed by dideoxynucleotide sequencing (United States Biochemical Corp. SEQUENASE kit, Cleveland, Ohio), was predicted, on the basis of the published L-1 DNA sequence of AcMNPV [Possee et al., (1991) *Virology* 185:229–241], to cause premature termination of 603 ORF translation at a site fourteen amino acids downstream of the deletion.

Example 3
Virus Bioassays

Polyhedral inclusion bodies (PIBs) of L-1, V-8, vEcoRIHybI, and vEcoRIHybIFS were prepared simultaneously from infected *Trichoplusia ni* larvae as previously described (O'Reilly et al., 1992). $LC_{50}$ data (the concentration of virus [PIBs/ml of diet] required for one half of the larvae to die by ten days post infection) and $LT_{50}$ data (the time taken, at a specific viral concentration, for one half of the larvae to die) were collected from neonate bioassays performed on *Spodoptera frugiperda* larvae. Neonates were allowed to feed for 24 hours on diet containing various concentrations of PIBs from the viruses being assayed and then transferred to individual cups containing diet without virus. The seven doses of each virus assayed were $5\times10^4$, $2\times10^5$, $5\times10^5$, $1\times10^6$, $2\times10^6$, $5\times10^6$, and $2\times10^7$ PIBs/ml. Sixty larvae were assayed per dose. Larval mortality was recorded at 48, 72, 84, 90, 96, 102, 108, 120, 132, and 144 hours post infection (p.i.). A final mortality count was performed at ten days post infection. $LT_{50}$ and $LC_{50}$ values were determined using probit analysis (Daum (1970) *Bulletin of the Entomological Soc. of America* 16:10–15).

Alternate virulence testing was done as follows: Trays were purchased from C-D International, Inc., and contained 32 separate arenas per tray. Each 4×4 cm (16 cm$^2$) arena contained 5 ml of appropriate artificial diet. Clear vented adhesive tops from C-D International, Inc., enclosed the insect in the arena following treatment and infestation. These clear tops allowed for easy scoring. The surface of the Stoneville (soybean/wheat germ diet) or pinto bean (Bio-Serv, Inc., Frenchtown, N.J. Diet #9393) diet was contaminated with 0.4 ml of aqueous viral solution. The dilutions ranged from $1\times10^8$ to $1\times10^1$ PIBs/ml, in 10-fold dilutions, depending upon the insect species tested. The applications were evenly distributed by rotating the tray and solutions were allowed to dry in a laminar flow hood. Bioassay trays were held at 28° C. in continuous fluorescent light throughout the study period. Readings were taken twice a day to observe early onset time of infection. $LC_{50}$ values were calculated from the BASIC log/probit statistics package and based on mortality versus dose at 8 days post-treatment. The $T_0$ (time at 0 hours) was based on initial average time when the larva was exposed to the treated diet. The $LT_{50}$ value was calculated from the BASIC log/probit statistics package based on mortality versus hours. The $LT_{50}$ data calculated were derived from the $LD_{95}$ value (based on a dose that was preferably less than 2 logs greater than the $LC_{50}$ value).

Example 4
Recombinant Virus Construction

Recombinant viruses are prepared essentially as described in O'Reilly et al. (1992) supra. The recombinant viruses vEcoRIHybI and vEcoRIHybIFS were constructed by cotransfecting SF-21 cells with vSynVI⁻gal DNA (Wang et al. (1991) *Gene* 100:131–137) and either pUC19HybI plasmid DNA (for vEcoRIHybI) or pUC19HybIFS plasmid DNA (for vEcoRIHybIFS (See Example 2). The virus vSynVI⁻gal expresses the *E. coli* lacZ gene instead of the polyhedrin gene and forms occlusion negative (OCC⁻), blue plaques in the presence of the chromogenic β-galactosidase indicator X-gal. Both pUC19HybI and pUC19HybIFS contain a polyhedrin gene; thus recombination between plasmid DNA derived from the polyhedrin region and viral DNA produced white occlusion positive (OCC$^+$) viral plaques. Viruses forming white OCC$^+$ plaques have lost the lacZ gene and acquired a functional polyhedrin gene through allelic replacement.

Example 5
Field Testing of Variant Baculovirus

The field trial program evaluates the efficacy of V8vEGTDEL relative to AcMNPV wild-type against important lepidopteran pests which attack vegetables. Pest organisms targeted in these field trials include cabbage looper, *Trichoplusia ni*; beet armyworm, *Spodoptera exigua*; fall armyworm, *Spodoptera frugiperda*; southern armyworm, *Spodoptera eridania*; tobacco budworm, *Heliothis virescens*; corn earworm, *Helicoverpa zeap*, diamondback moth, *Plutella xylostella*; cabbageworm, *Pieris rapae*. Each test is conducted on land currently used for growth/production of row crops (i.e., commercial or research farms). The crop used in each test is a leafy vegetable (e.g., lettuce) or a crucifer (e.g., cabbage). Each field trial consists of the following eight treatments: V8vEGTDEL (see Examples 6 and 7 hereinbelow) at $1 \times 10^9$, $10^{11}$, and $10^{13}$ PIBs/acre; AcMNPV at $1 \times 10^9$, $10^{11}$, and $10^{13}$ PIBs/acre, and untreated control. Within a given test, each treatment will be applied to the crop no more than six (6) times; treatments will be applied on an "as needed" basis (i.e., as pest populations warrant, probably 5- to 14-day intervals).

Within each test, there is a maximum of six applications of each treatment. Treatments are applied to plots in each test by using ground equipment, either small tractor sprayers or $CO_2$-driven backpack sprayers. Treatments are diluted in water and applied through standard agricultural hydraulic spray booms and nozzles. The maximum size of a treatment plot (i.e., replicate) in each test is 0.018 acres (i.e., 4 rows wide×60 ft. long, row spacing of 40 in.). The maximum number of plots (i.e., replicates) per treatment in each test is four. Each test is monitored on at least a weekly basis for the duration of the study. Each of these trials will be conducted on secured private farm land or research farms (no trespassing by unauthorized individuals). At the conclusion of each test, the test area and a 10 ft.-wide untreated test perimeter undergo "crop destruction" (i.e., rather than being harvested for commercial use, the treated and adjacent crop is shredded and plowed underground).

Soil is perhaps the most important reservoir for persistence of virus in the environment. The monitoring program consists of the collection of 4 soil samples (each 7.6 cm in depth) totaling 500 g from within the test site and from an area 100 ft outside the treatment zone. Samples are taken approximately midway through the test. A second set of samples are collected at the end of the test after all disinfection procedures (as described below) have been completed.

Monitoring for viable, infectious virus is important because immunodetection and PCR methods make no distinction between infectious occlusion bodies and non-viable remnants of viral particles. The only reliable method for determining if viable, infectious viral particles are present in the soil samples is to perform bioassays of the samples on a highly susceptible insect host such as *Heliothis virescens*. From each 500 g sample of soil, 25 g is used in the bioassay. A standard method for isolation of viral occlusion bodies from soil is used. This method efficiently recovers approximately 46% of polyhedra from soil. The $LC_{50}$ for AcMNPV in our standard diet overlay assay is 300–1000 polyhedra/arena for *H. virescens*. Therefore, if each larvae to be bioassayed is fed the isolate from 1 g of soil this assay reliably detects 600–2000 viral occlusion bodies per gram of assayed soil. Larvae which exhibit typical symptoms of viral infection in the bioassay are examined for the presence of occlusion bodies using light microscopy. If polyhedra are observed, they are isolated from the cadaver for DNA isolation from the occlusion bodies and a standard PCT assay (routinely performed in the lab) is done using primers flanking the vEGTDEL deletion (See FIG. 6, e.g.). The efficiency of DNA recovery and the PCR assay approaches 100%. If the virus present is vEGTDEL, then a DNA fragment of a characteristic size is observed, allowing unambiguous identification of the virus as vEGTDEL. Other viruses generate DNA fragments of differing sizes.

AcMNPV variants having deletions in the egt gene can arise spontaneously in nature, and such viruses ares subject to a severe replicative disadvantage that will not allow them to compete effectively with indigenous viruses in the environment. Furthermore, since egt-inactivated virus produce 30%–50% fewer polyhedra following a successful infection, environmental persistence is further compromised. Contaminated plants within the test site and 10 ft.-wide buffer, tools, and farm implements are topically sterilized with a 1% bleach wash to prevent unnecessary dispersal of the viral insecticide.

The V8vEGTDEL formulation for the field trial program is in the form of a wettable powder. On a weight:weight basis, ingredients of this formulation are as follows:

|  | % Weight |
|---|---|
| V8vEGTDEL | 10.00 |
| EUDRAGIT S100 | 0.45 |
| UV-9 oxybenzone | 2.50 |
| polyethylene glycol MW400 | 0.10 |
| MIRASPERSE | 39.10 |
| REAX ATN lignin sulfonate | 4.90 |
| 10X Sugar | 19.45 |
| MOREWET EFW | 19.60 |
| MICROCEL E | 3.90 |
|  | 100.00 |

EUDRAGIT S100 (Rohm Pharma Co.) comprises methyl methacrylic and methyl methacrylate. It is a pH dependent coating agent which holds UV9 on the PIBs, and it slightly prolongs photostability of the formulation. UV-9 oxybenzone (Cytech Ind.) also provides slight photostability to the formulation. Polyethylene glycol MW400 (Aldrich Chemical Co.) provides flexibility to the UV-protectant coatings. MIRASPERSE (Staley Co.) is a starch-based "sticker," and provides rainfastness to the formulation after it is applied to the crop. REAX ATN (West Waco Co.) is a lignin sulfonate, and it is used as a dispersant and keeps the particles separate in the liquid phase (i.e., in the water diluent). Sugar is used as an insect feeding stimulant and/or attractant. MOREWET EFW (Witco Co.) is a wetting agent, so that the formulation can more effectively spread across the surface of a treated leaf. MICROCEL E (Manville Co.) is a clay-based flow agent that prevents the wettable powder from caking during storage.

For use in the test formulations, the PIBs (polyhedrin inclusion bodies) are air-milled to under 10 μm in size, and coated with an organic solution containing EUDRAGIT S100, UV-9, and MW400. The other aforementioned inerts are blended and Fitz-milled to make a pre-blend. The coated PIBs and the pre-blend are blended together and Fitz-milled, and then the formulation is packaged. No extraneous microorganisms will be present in the formulation since production in tissue culture requires the use of sterile procedures. In each 10 g of wettable powder formulation, there is 1 g ($2 \times 10^{11}$ PIBs) of V8vEGTDEL.

A preferred wettable powder insecticidal composition is as follows:

| Ingredient | Nominal Percent (w/w) |
|---|---|
| V8vEGTDEL polyhedrin inclusion bodies | 10.0% |
| MORWET D245 | 30.0% |
| MOREWET EFW | 20.0% |
| Kaolin Clay | 16.0% |
| MICROCEL E | 16.0% |
| UV-9 oxybenzone or charcoal | 5.0% |
| EUDRAGIT S100 | 2.0% |
| Citric Acid | 0.9% |
| polyethylene glycol MW400 | 0.1% |

The active ingredient is V8vEGTDEL. Morewet D425 is used as a dispersant and keeps the particles separate in the liquid phase (i.e., in the water diluent). MOREWET EFW (Witco Co.) is a wetting agent, so that the formulation can more effectively spread across the surface of a treated leaf. Kaolin Clay is a bulking agent. MICROCEL E (Manville Co.) is a flow agent that prevents the wettable powder from caking. UV-9 (or charcoal) provides slight photostability to the formulation. EUDRAGIT S100 (Rohm Pharma Co.) also slightly prolongs photostability of the formulation. Citric acid is used for pH adjustment. MW400 (Aldrich Chemical Co.) provides flexibility to the UV-protectant coatings.

A stilbene brightener is optionally added (at approximately 5% w/w) to PIBs in alternative preferred wettable powder formulations, and the percentages of other inert ingredients are then adjusted accordingly. Stilbenes provide some protection against UV inactivation and can also serve to enhance or potentiate virus infectivity, particularly in insects which are less susceptible to the insect virus, see, e.g., U.S. Pat. No. 5,246,936 (issued Sep. 21, 1993, Treacy et al.), which is incorporated by reference herein.

In this formulation the PIBs are first coated using an aqueous coating procedure. A 1% (w/v) suspension of EUDRAGIT S100 is prepared in water. The EUDRAGIT is dissolved by adjusting the pH to between 9.0 and 9.5. Viral PIBs, BLANKPHOR BBH (stilbene brightner, Miles Inc; if used), and UV-9 oxybenzone or charcoal in the proper proportions are added. The mixture is blended to create an even suspension and then air-dried. The dried coated PIBs are then air-milled to achieve a small particle size. This material is then dry blended with the prescribed amounts of MORWET 425, MOREWET EFW, Kaolin Clay, MICROCEL E, Citric acid and polyethylene glycol MW400 and then packaged as the final formulation. The preferred particle size of the blended material is less than 20 $\mu$m.

Example 6

Figure 1B:
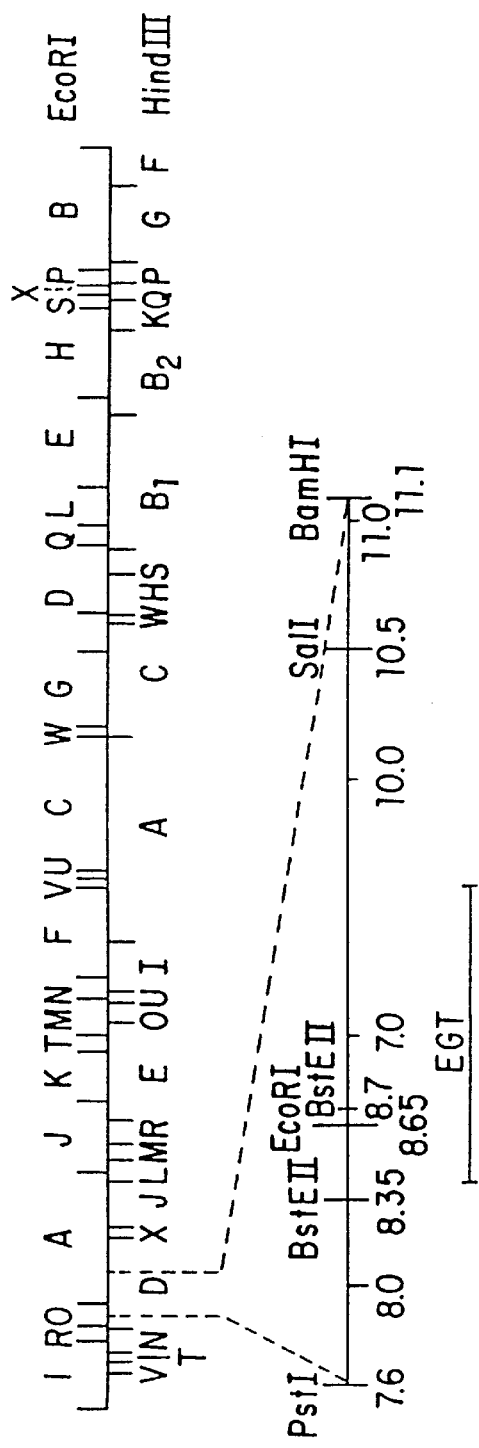
FIG. 1B is an enlargement of the AcMNPV genome from 7.6 to 11.1 map units.
Figure 1C:
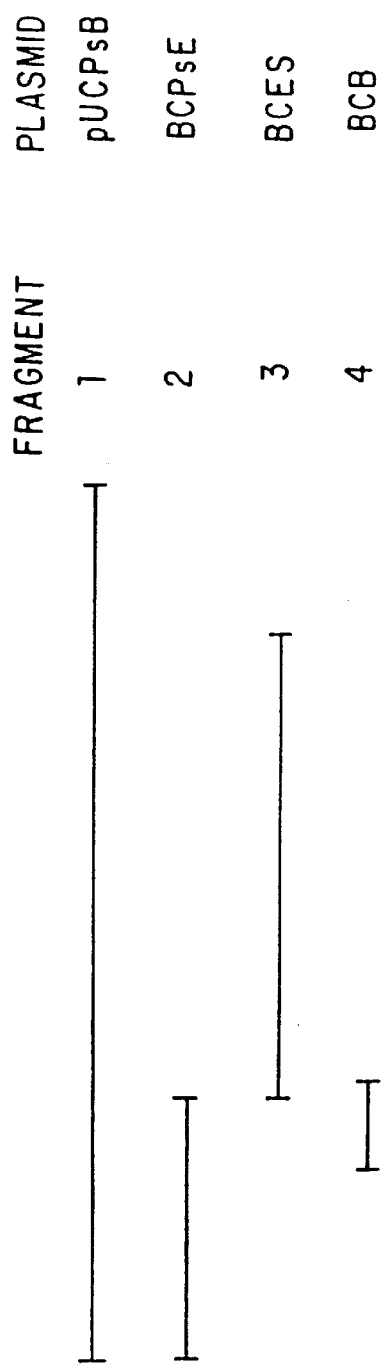
FIG. 1C shows certain cloned AcMNPV L-1 DNA fragments and the resulting plasmids.
Figures 2A, 2B:
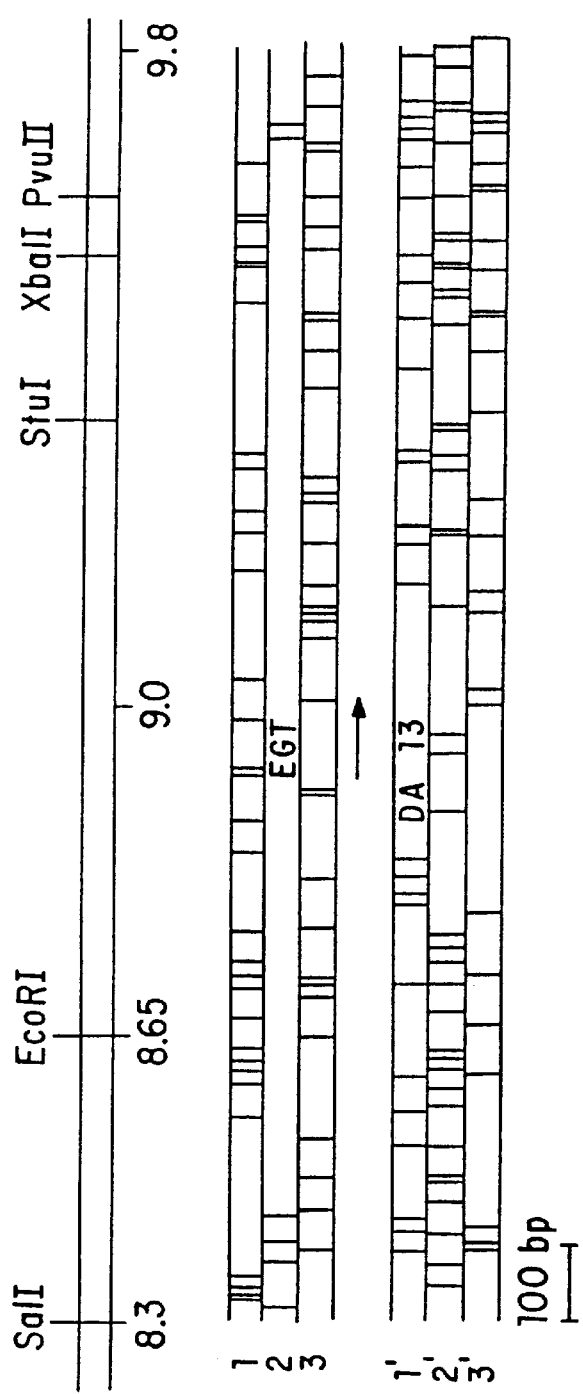
FIG. 2A is a schematic representation of the structures of the egt gene region of AcMNPV with restriction sites.
FIG. 2B shows the location of the egt gene.
Figure 3A:
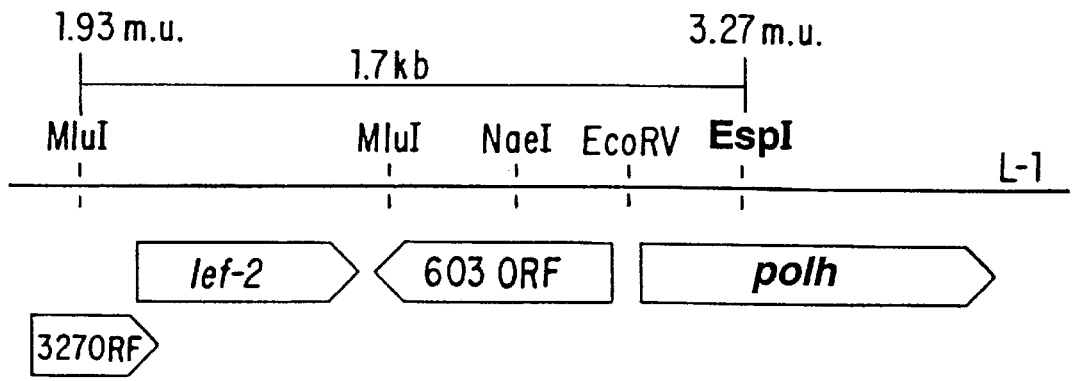
FIGS. 3A–3D represents partial restriction maps of the 327 ORF, lef-2, the 603 ORF, and the polyhedrin gene (polh) region of AcMNPV strains.
Figure 3B:
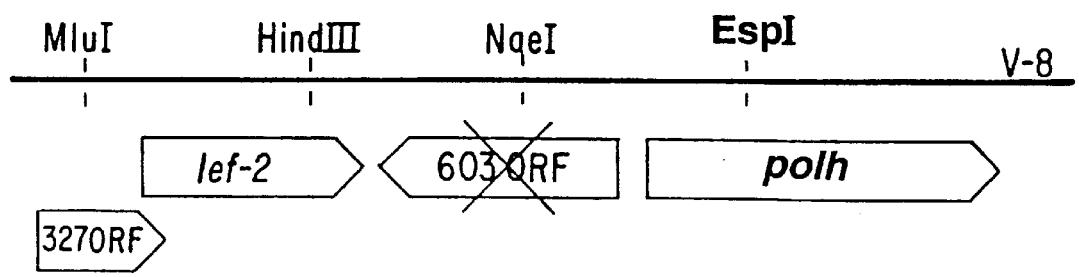
Figure 3C:
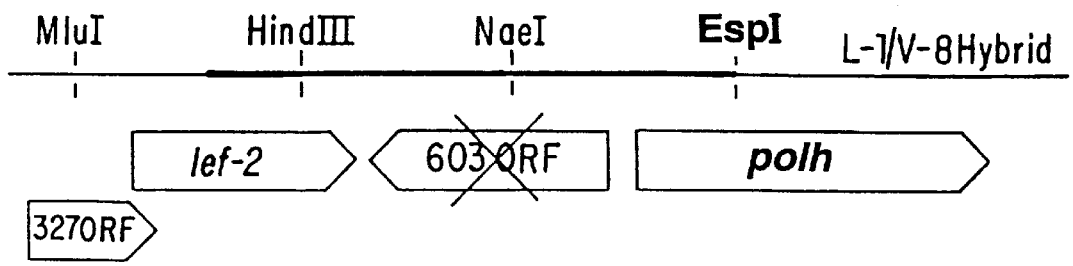
Figure 3D:
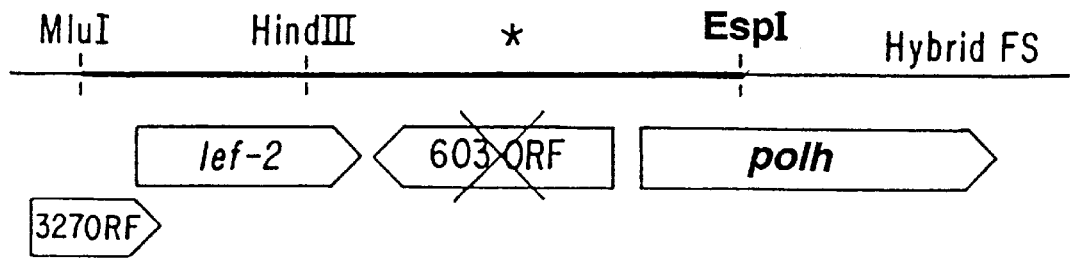

The position of the egt gene on the AcMNPV genome is illustrated in FIG. 2B. A scale in map units is presented above the map of the AcMNPV genome in FIG. 1A. The nucleotide sequence of the AcMNPV L-1 egt gene and flanking regions has been determined (FIGS. 6A–6B, SEQ ID NO:5). FIG. 1A shows a linear map of the AcMNPV L-1 genome after cleavage with restriction endonucleases EcoRI and HindIII. FIG. 1B is an enlargement of the AcMNPV genome from 7.6 to 11.1 map units showing the location of the egt gene. The AcMNPV strain L-1 has been described (Lee and Miller (1978) J. Virol. 27:754). Cloned L-1 DNA fragments and the names of the resultant plasmids are shown in FIG. 1C. Fragment 1, which extends from the PstI site at 7.6 mu to a BamHI site at 11.1 mu, is cloned into the plasmid vector pUC19; fragments 2 and 3 (from PstI (7.6 mu) to EcoRI (8.65 mu) and from EcoRI (8.65 mu) to SalI (10.5 mu), respectively) are both cloned into the vectors Bluescript M13+ and Bluescript M13– (Stratagene, San Diego, Calif.). Fragment 5 (BstEII (8.35 mu) to BstEII (8.7 mu) is cloned into Bluescript M13+.

The nucleotide sequence of the egt gene is presented in SEQ ID NO:6 and in SEQ ID NO:5 from nucleotide 149 to nucleotide 1669.

Example 7

To construct AcMNPV recombinant viruses (e.g., V-8) incapable of expressing a functional egt gene, further manipulation of the plasmid clones described in Example I is required. Plasmid pUCBCPsB is cleaved with restriction endonucleases EcoRI and XbaI (see FIG. 3 for sites within the egt gene) and the small fragment is discarded. The *Escherichia coli* lacZ gene, excised from pSKS104 (Casadaban et al. (1983) *Methods Enzymol.* 100:293–303) with EcoRI and AhaIII, is then inserted between the EcoRI and XbaI sites after the XbaI overhanging ends are filled in using T4 DNA polymerase. The resultant plasmid is designated pEGTZ. In this plasmid, the inserted lacZ gene is in frame with the preceding egt coding sequences. Alternatively, the plasmid pEGTDEL is constructed by simply ligating the EcoRI and XbaI sites together (after both sites have been blunt-ended) without inserting any sequences between them.

Plasmid pEGTZ is then cotransfected with AcMNPV V-8 DNA into SF cells as described in Miller et al. (1986) supra. This procedure allows for homologous recombination to take place between sequences in the viral and plasmid DNAs, resulting in replacement of the viral egt gene with the egt-lacZ gene fusion from the plasmid. Because the remaining egt coding sequence is in frame with the lacZ sequences, such a recombinant virus will produce a fusion protein comprising the first 84 amino acids of egt joined to β-galactosidase. The recombinant virus, termed vEGTZ, can be identified because β-galactosidase expression gives rise to blue viral plaques in the presence of a chromogenic indicator such as 5-bromo-4-chloro-3-indolyl-β-D-galactopyranoside (X-gal).

Recombinant virus V8vEGTDEL is obtained by cotransfecting the plasmid pEGTDEL and DNA from the virus vEGTZ into SF cells. Homologous recombination results in the replacement of the egt-lacZ fusion gene in V8vEGTZ with the deleted egt gene from pEGTDEL. The recombinant virus V8vEGTDEL is identified by its failure to form blue plaques in the presence of X-gal.

In a specific embodiment of an AcMNPV V-8 virus in which the egt is inactivated, a DNA fragment from 7.6–11.1 map units on the physical map of AcMNPV was cloned into a plasmid vector as described in U.S. Pat. No. 5,180,581, incorporated by reference herein.

This AcMNPV fragment contains the egt gene and flanking viral DNA. An internal deletion was made in the egt gene and the *E. coli* lacZ gene was fused in frame. The initial egt-deleted virus, designated vEGTZ, was constructed using this fusion plasmid to replace the egt gene in AcMNPV by allelic recombination mediated by cellular recombination mechanisms. Presence of a functional lacZ gene facilitated the identification of the recombinant virus by its blue color in plaque assays in the presence of an appropriate chromogenic indicator. An additional egt-deleted virus, vEGTDEL, was constructed by deleting an internal portion of the egt gene from the plasmid vector containing the 7.6–11.1 map unit region of the AcMNPV genome using PCR mediated mutagenesis. The sequence of the egt coding region and flanking sequences are shown in FIGS. 6A–6B, along with the locations of the PCR primers. Deletion at the precise sites indicated in FIG. 3 results in the formation of two novel and easily characterized restriction enzyme sites (EcoRI and XhaI) at the deletion junction. This deletion plasmid was then used to replace the egt-deleted lacZ gene.

Example 8

EGT enzymatic activity protein can be determined as follows: SF cells are infected with AcMNPV as described hereinbefore. Twelve hours post infection the cells and extracellular media are collected and processed separately. Uninfected cells are treated in parallel. Cell lysates or extracellular media are incubated in the presence of 1 mM UDP-glucose, UDP-galactose and 0.25 µCi[$^3$H]ecdysone as described in O'Reilly and Miller (1989) *Science* 1110–1112. Ecdysteriod UDP-glucosyl transferase activity in the cell lysates or media catalyze the transfer of glucose from the UDP-glucose to ecdysone to form an ecdysone-glucose conjugate. Ecdysone and the ecdysone-sugar conjugate are separated from one another by silica gel thin layer chromatography (Bansal and Gessner (1988) *Anal. Biochem.* 109:321) and visualized by autoradiography. Ecdysone-glucose conjugates (G) are only formed when wt AcMNPV-infected cell lysate or extracellular medium is assayed. No conjugates are observed when uninfected or egt-inactivated virus infected cell lysates or media are used, showing that the activity is due to egt expression. Most of the activity is located in the extracellular medium.

It should be understood that the foregoing relates only to preferred specific embodiments of the present invention and that numerous modifications or alterations may be made therein without departing from the spirit and the scope of the invention as set forth in the appended claims.

We claim:

1. An isolated DNA molecule comprising a nucleotide sequence as given in FIG. 4 from nucleotide 3002 to 4231, V-8 sequence, (nucleotides 534 to 1763 in SEQ ID NO:3), wherein said nucleotide sequence confers improved killing properties for at least one insect pest when said nucleotide sequence is incorporated in a Baculovirus genome.

2. The isolated DNA molecule of claim 1 comprising the nucleotide sequence as given in FIG. 4 from nucleotide 2469 to 4231 (SEQ ID NO:3).

3. A Baculovirus having improved killing properties for at least one insect pest, said Baculovirus being genetically engineered to contain the nucleotide sequence of claim 1, wherein said insect virus is not an *Autographa californica* nuclear polyhedrosis virus.

4. The Baculovirus of claim 1 which is a nuclear polyhedrosis virus or a granulosis virus.

5. The Baculovirus of claim 4 wherein said baculovirus is a nuclear polyhedrosis virus.

6. The Baculovirus of claim 3 which has been further genetically engineered to inactivate a gene encoding ecdysteroid glucosyltransferase.

7. The baculovirus of claim 6 in which said ecdysteroid glucosyltransferase gene has been inactivated by deleting at least a portion thereof.

8. An isolated and purified recombinant baculovirus having incorporated within its genome a segment of heterologous insect virus DNA conferring improved killed properties, which recombinant baculovirus effects faster killing for at least one insect pest as compared with an isogenic parental baculovirus lacking said segment of DNA wherein said baculovirus is not *Autographa californica* Nuclear Polyhedrosis Virus.

9. The recombinant baculovirus of claim 8 wherein said segment of DNA comprises V-8 sequences, nucleotides 3002 to 4231 as shown in FIG. 4 (nucleotides 534 to 1763 in SEQ ID NO:3).

10. The recombinant baculovirus of claim 8 wherein said segment of DNA comprises V-8 sequence, nucleotides 2469 to 4231 as shown in FIG. 4 (nucleotides 1 to 1763 in SEQ ID NO:3).

11. The baculovirus of claim 8 which has been further improved as an insect control agent by inactivating a gene encoding ecdysteroid glucosyltransferase.

12. An insecticidal composition comprising an effective amount of the baculovirus of claim 8 and a suitable carrier.

13. The insecticidal composition of claim 12 wherein said improved killing properties of the baculovirus are determined by a shorter time between infection of neonate larvae of said insect pest and the time when half of the infected larvae are dead than is observed for the comparison baculovirus.

14. The insecticidal composition of claim 13 wherein said baculovirus has been genetically engineered to inactivate a gene encoding ecdysteroid UDP-glucosyltransferase.

\* \* \* \* \*

UNITED STATES PATENT AND TRADEMARK OFFICE
CERTIFICATE OF CORRECTION

PATENT NO. : 5,858,353

DATED : January 12, 1999

INVENTOR(S) : Miller et al.

It is certified that error appears in the above-indentified patent and that said Letters Patent is hereby corrected as shown below:

At Col. 7, line 29, replace "NO:6" with --NO:8--, and replace "NO:7" with --NO:9--.

At Col. 7, line 30, replace "NO:8" with --NO:10--.

At Col. 8, line 55, replace "FIG. 2" with --FIG. 3--.

At Col. 10, line 24, replace "$L_{90}$" with --$LC_{90}$--.

At Col. 11, below line 41, insert --TABLE 2--.

At Col. 14, line 20, delete ")" after "1333".

At Col. 17, line 15, replace "10 $^E9$" with --$10^9$--.

At Col. 19, line 27, replace "agar-ased" with --agar-based--.

At Col. 20, line 52, replace "$LD_{95}$" with --$LC_{90}$--.

At Col. 22, line 7, rewrite "PCT" as --PCR--.

At Col. 24, line 9, please delete "nucleotide" and insert --amino acid--.

In the claims:

In Claim 4, replace "claim 1" with --claim 3--.

Signed and Sealed this

Fifth Day of October, 1999

Q. TODD DICKINSON

*Attest:*

*Attesting Officer*   Acting Commissioner of Patents and Trademarks

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 1721 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 194..826

( x i ) SEQUENCE DESCRIPTION: SEQ ID NO:1:

```
ACGCGTTCCG  GCACGAGCTT  TGATTGTAAT  AAGTTTTTAC  GAAGCGATGA  CATGACCCCC        60

GTAGTGACAA  CGATCACGCC  CAAAAGAACT  GCCGACTACA  AAATTACCGA  GTATGTCGGT       120

GACGTTAAAA  CTATTAAGCC  ATCCAATCGA  CCGTTAGTCG  AATCAGGACC  GCTGGTGCGA       180

GAAGCCGCGA  AGT  ATG  GCG  AAT  GCA  TCG  TAT  AAC  GTG  TGG  AGT  CCG  CTC       229
             Met  Ala  Asn  Ala  Ser  Tyr  Asn  Val  Trp  Ser  Pro  Leu
              1                  5                         10

ATT  AGA  GCG  TCA  TGT  TTA  GAC  AAG  AAA  GCT  ACA  TAT  TTA  ATT  GAT  CCC    277
Ile  Arg  Ala  Ser  Cys  Leu  Asp  Lys  Lys  Ala  Thr  Tyr  Leu  Ile  Asp  Pro
          15                    20                        25

GAT  GAT  TTT  ATT  GAT  AAA  TTG  ACC  CTA  ACT  CCA  TAC  ACG  GTA  TTC  TAC    325
Asp  Asp  Phe  Ile  Asp  Lys  Leu  Thr  Leu  Thr  Pro  Tyr  Thr  Val  Phe  Tyr
     30                    35                       40

AAT  GGC  GGG  GTT  TTG  GTC  AAA  ATT  TCC  GGA  CTG  CGA  TTG  TAC  ATG  CTG    373
Asn  Gly  Gly  Val  Leu  Val  Lys  Ile  Ser  Gly  Leu  Arg  Leu  Tyr  Met  Leu
45                      50                       55                      60

TTA  ACG  GCT  CCG  CCC  ACT  ATT  AAT  GAA  ATT  AAA  AAT  TCC  AAT  TTT  AAA    421
Leu  Thr  Ala  Pro  Pro  Thr  Ile  Asn  Glu  Ile  Lys  Asn  Ser  Asn  Phe  Lys
                     65                      70                      75

AAA  CGC  AGC  AAG  AGA  AAC  ATT  TGT  ATG  AAA  GAA  TGC  GTA  GAA  GGA  AAG    469
```

```
Lys Arg Ser Lys Arg Asn Ile Cys Met Lys Glu Cys Val Glu Gly Lys
                80                  85                  90

AAA AAT GTC GTC GAC ATG CTG AAC AAC AAG ATT AAT ATG CCT CCG TGT        517
Lys Asn Val Val Asp Met Leu Asn Asn Lys Ile Asn Met Pro Pro Cys
            95                  100                 105

ATA AAA AAA ATA TTG AAC GAT TTG AAA GAA AAC AAT GTA CCG CGC GGC        565
Ile Lys Lys Ile Leu Asn Asp Leu Lys Glu Asn Asn Val Pro Arg Gly
        110                 115                 120

GGT ATG TAC AGG AAG AGG TTT ATA CTA AAC TGT TAC ATT GCA AAC GTG        613
Gly Met Tyr Arg Lys Arg Phe Ile Leu Asn Cys Tyr Ile Ala Asn Val
125                 130                 135                 140

GTT TCG TGT GCC AAG TGT GAA AAC CGA TGT TTA ATC AAG GCT CTG ACG        661
Val Ser Cys Ala Lys Cys Glu Asn Arg Cys Leu Ile Lys Ala Leu Thr
                145                 150                 155

CAT TTC TAC AAC CAC GAC TCC AAG TGT GTG GGT GAA GTC ATG CAT CTT        709
His Phe Tyr Asn His Asp Ser Lys Cys Val Gly Glu Val Met His Leu
            160                 165                 170

TTA ATC AAA TCC CAA GAT GTG TAT AAA CCA CCA AAC TGC CAA AAA ATG        757
Leu Ile Lys Ser Gln Asp Val Tyr Lys Pro Pro Asn Cys Gln Lys Met
        175                 180                 185

AAA ACT GTC GAC AAG CTC TGT CCG TTT GCT GGC AAC TGC AAG GGT CTC        805
Lys Thr Val Asp Lys Leu Cys Pro Phe Ala Gly Asn Cys Lys Gly Leu
190                 195                 200

AAT CCT ATT TGT AAT TAT TGA ATAATAAAC AATTATAAAT GCTAAATTTG            856
Asn Pro Ile Cys Asn Tyr  *
205                 210

TTTTTTATTA ACGATACAAA CCAAACGCAA CAAGAACATT TGTAGTATTA TCTATAATTG      916

AAAACGCGTA GTTATAATCG CTGAGGTAAT ATTTAAAATC ATTTTCAAAT GATTCACAGT      976

TAATTTGCGA CAATATAATT TTATTTTCAC ATAAACTAGA CGCCTTGTCG TCTTCTTCTT     1036

CGTATTCCTT CTCTTTTTCA TTTTTCTCCT CATAAAAATT AACATAGTTA TTATCGTATC     1096

CATATATGTA TCTATCGTAT AGAGTAAATT TTTTGTTGTC ATAAATATAT ATGTCTTTTT     1156

TAATGGGGTG TATAGTACCG CTGCGCATAG TTTTTCTGTA ATTTACAACA GTGCTATTTT     1216

CTGGTAGTTC TTCGGAGTGT GTTGCTTTAA TTATTAAATT TATATAATCA ATGAATTTGG     1276

GATCGTCGGT TTTGTACAAT ATGTTGCCGG CATAGTACGC AGCTTCTTCT AGTTCAATTA     1336

CACCATTTTT TAGCAGCACC GGATTAACAT AACTTTCCAA AATGTTGTAC GAACCGTTAA     1396

ACAAAAACAG TTCACCTCCC TTTTCTATAC TATTGTCTGC GAGCAGTTGT TTGTTGTTAA     1456

AAATAACAGC CATTGTAATG AGACGCACAA ACTAATATCA CAAACTGGAA ATGTCTATCA     1516

ATATATAGTT GCTGATATCA TGGAGATAAT TAAATGATA ACCATCTCGC AAATAAATAA      1576

GTATTTACT GTTTCGTAA CAGTTTTGTA ATAAAAAAC CTATAAATAT GCCGGATTAT        1636

TCATACCGTC CCACCATCGG GCGTACCTAC GTGTACGACA ACAAGTACTA CAAAAATTTA     1696

GGTGCCGTTA TCAAGAACGC TAAGC                                          1721
```

( 2 ) INFORMATION FOR SEQ ID NO:2:

( i ) SEQUENCE CHARACTERISTICS:
        ( A ) LENGTH: 210 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ala Asn Ala Ser Tyr Asn Val Trp Ser Pro Leu Ile Arg Ala Ser
1               5                   10                  15
```

|   |   |   |   |   |   |   |   |   |   |   |   |   |   |
|---|---|---|---|---|---|---|---|---|---|---|---|---|---|
| Cys | Leu | Asp | Lys<br>20 | Lys | Ala | Thr | Tyr<br>25 | Leu | Ile | Asp | Pro | Asp<br>30 | Phe | Ile |
| Asp | Lys | Leu<br>35 | Thr | Leu | Thr | Pro | Tyr<br>40 | Thr | Val | Phe | Tyr | Asn<br>45 | Gly | Gly | Val |
| Leu | Val<br>50 | Lys | Ile | Ser | Gly | Leu<br>55 | Arg | Leu | Tyr | Met | Leu<br>60 | Leu | Thr | Ala | Pro |
| Pro<br>65 | Thr | Ile | Asn | Glu | Ile<br>70 | Lys | Asn | Ser | Asn | Phe<br>75 | Lys | Lys | Arg | Ser | Lys<br>80 |
| Arg | Asn | Ile | Cys | Met<br>85 | Lys | Glu | Cys | Val | Glu<br>90 | Gly | Lys | Lys | Asn | Val<br>95 | Val |
| Asp | Met | Leu | Asn<br>100 | Asn | Lys | Ile | Asn | Met<br>105 | Pro | Pro | Cys | Ile | Lys<br>110 | Lys | Ile |
| Leu | Asn | Asp<br>115 | Leu | Lys | Glu | Asn | Asn<br>120 | Val | Pro | Arg | Gly | Gly<br>125 | Met | Tyr | Arg |
| Lys | Arg<br>130 | Phe | Ile | Leu | Asn | Cys<br>135 | Tyr | Ile | Ala | Asn | Val<br>140 | Val | Ser | Cys | Ala |
| Lys<br>145 | Cys | Glu | Asn | Arg | Cys<br>150 | Leu | Ile | Lys | Ala | Leu<br>155 | Thr | His | Phe | Tyr | Asn<br>160 |
| His | Asp | Ser | Lys | Cys<br>165 | Val | Gly | Glu | Val | Met<br>170 | His | Leu | Leu | Ile | Lys<br>175 | Ser |
| Gln | Asp | Val | Tyr<br>180 | Lys | Pro | Pro | Asn | Cys<br>185 | Gln | Lys | Met | Lys | Thr<br>190 | Val | Asp |
| Lys | Leu | Cys<br>195 | Pro | Phe | Ala | Gly | Asn<br>200 | Cys | Lys | Gly | Leu | Asn<br>205 | Pro | Ile | Cys |
| Asn | Tyr<br>210 |

( 2 ) INFORMATION FOR SEQ ID NO:3:

( i ) SEQUENCE CHARACTERISTICS:
        ( A ) LENGTH: 1763 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 194..826

( x i ) SEQUENCE DESCRIPTION: SEQ ID NO:3:

```
ACGCGTTCCG GCACGAGCTT TGATTGTAAT AAGTTTTTAC GAAGCGATGA CATGACCCCC      60

GTAGTGACAA CGATCACGCC CAAAAGAACT GCCGACTACA AAATTACCGA GTATGTCGGT     120

GACGTTAAAA CTATTAAGCC ATCCAATCGA CCGTTAGTCG AATCAGGACC GCTGGTGCGA     180

GAAGCCGCGA AGT ATG GCG AAT GCA TCG TAT AAC GTG TGG AGT CCG CTC        229
            Met Ala Asn Ala Ser Tyr Asn Val Trp Ser Pro Leu
                215                         220

ATT AGC GCG TCA TGT TTA GAC AAG AAA GCT ACA TAT TTA ATT GAT CCC      277
Ile Ser Ala Ser Cys Leu Asp Lys Lys Ala Thr Tyr Leu Ile Asp Pro
225                 230                 235

GAT GAT TTT ATT GAT AAA TTG ACC CTA ACT CCA TAC ACG GTA TTC TAC      325
Asp Asp Phe Ile Asp Lys Leu Thr Leu Thr Pro Tyr Thr Val Phe Tyr
240                 245                 250                 255

AAT GGC GGG GTT TTG GTC AAA ATT TCC GGA CTG CGA TTG TAC ATG CTG      373
Asn Gly Gly Val Leu Val Lys Ile Ser Gly Leu Arg Leu Tyr Met Leu
```

```
                              260                           265                           270
TTA  ACG  GCT  CCG  CCC  ACT  ATT  AAT  GAA  ATT  AAA  AAT  TCC  AAT  TTT  AAA               421
Leu  Thr  Ala  Pro  Pro  Thr  Ile  Asn  Glu  Ile  Lys  Asn  Ser  Asn  Phe  Lys
               275                      280                     285

AAA  CGC  AGC  AAG  AGA  AAC  ATT  TGT  ATG  AAA  GAA  TGC  GCA  GAA  GGA  AAG               469
Lys  Arg  Ser  Lys  Arg  Asn  Ile  Cys  Met  Lys  Glu  Cys  Ala  Glu  Gly  Lys
               290                      295                     300

AAA  AAT  GTC  GTT  GAC  ATG  CTG  AAC  AGC  AAG  ATC  AAT  ATG  CCT  CCG  TGT               517
Lys  Asn  Val  Val  Asp  Met  Leu  Asn  Ser  Lys  Ile  Asn  Met  Pro  Pro  Cys
     305                           310                     315

ATA  AAA  AAA  ATA  TTG  GGC  GAT  TTG  AAA  GAA  AAC  AAT  GTA  CCA  CGC  GGC               565
Ile  Lys  Lys  Ile  Leu  Gly  Asp  Leu  Lys  Glu  Asn  Asn  Val  Pro  Arg  Gly
320                           325                     330                     335

GGT  ATG  TAC  AGG  AAG  AGA  TTT  ATA  TTA  AAC  TGT  TAC  ATT  GCA  AAC  GTG               613
Gly  Met  Tyr  Arg  Lys  Arg  Phe  Ile  Leu  Asn  Cys  Tyr  Ile  Ala  Asn  Val
                    340                      345                     350

GTT  TCG  TGT  GCC  AAA  TGT  GAA  AAC  CGA  TGT  TTA  ATC  AAT  GCT  CTG  ACG               661
Val  Ser  Cys  Ala  Lys  Cys  Glu  Asn  Arg  Cys  Leu  Ile  Asn  Ala  Leu  Thr
               355                      360                     365

CAT  TTC  TAC  AAC  CAC  GAT  TCC  AAA  TGT  GTG  GGT  GAA  GTC  ATG  CAT  CTT               709
His  Phe  Tyr  Asn  His  Asp  Ser  Lys  Cys  Val  Gly  Glu  Val  Met  His  Leu
          370                           375                     380

TTA  ATT  AAA  TCC  CAA  GAT  GTT  TAT  AAA  CCA  CCA  AAC  TGC  CAA  AAA  ATG               757
Leu  Ile  Lys  Ser  Gln  Asp  Val  Tyr  Lys  Pro  Pro  Asn  Cys  Gln  Lys  Met
     385                           390                     395

AAA  AAT  GTC  GAC  AAG  CTT  TGC  CCG  TTT  GCT  GGC  AAC  TGC  AAG  GGT  CTC               805
Lys  Asn  Val  Asp  Lys  Leu  Cys  Pro  Phe  Ala  Gly  Asn  Cys  Lys  Gly  Leu
400                           405                     410                     415

AAT  CCT  ATT  TGT  AAT  TAT  TGA  ATAATAAAC  AATTATAAAT  GCTAAATTTG                          856
Asn  Pro  Ile  Cys  Asn  Tyr  *
                    420

TTTTTTATTA  ACGATACAAA  CCAAACGCAA  CAAGAACATT  TGTAGAATTA  TCTATAATTG                        916

AAAACGCATA  ATTATAATCG  TCAAGGTAAT  GTTTAAAATC  ATTTTCAAAT  GATTCACAGT                        976

TAATTTGCGA  CAGTATAATT  TTGTTTTCAC  ATAAACTAGA  CGCCTTTATC  TGTCTGTCGT                       1036

CTTCTTCGTA  TTCTTTTTCT  TTTTCATTTT  TCTCTTCATA  AAAATTCACA  TAATTATTAT                       1096

CGTATCCATA  TATGTATCTG  TCGTAAAGAG  TAAATTTTTT  GTTGTCATAA  ATATATATGT                       1156

CTTTTTTAAT  GGGGTGTATA  GTACCGCTGC  GCATAGTTTT  TCTTTAATTT  AAACCAGTGC                       1216

TATTTCTGG   TAATTCTTCG  GAGTGTGTTG  CTTTAATTAT  TAAATTTATA  TAATCAATGA                       1276

ATTTGGGATC  GTCGGTTTTG  TACAATATGT  TGCCGGCATA  GTACGCAGCT  GGCTCTAAAT                       1336

CAATATTTTT  TAAACAACGA  CTGGATCAAC  ATTACCATTT  TTTAGCAACA  CTGGATTAAC                       1396

ATAATTTTCC  AAAATGCTGT  ACGAAGCGTT  TAACAAAAAC  AGTTCACCTC  CGTTTTCTAT                       1456

ACTATCGTCT  GCGAGCAGTT  GCTTGTTGTT  AAAAATAACG  GCCATTGTAA  TGAAACGCAC                       1516

AAACTAATAT  TACACACTAA  AAAAATCTAT  CATTTCGGCT  TAATATATAG  TTGCTGATAT                       1576

TATGTAAATA  ATTAAAATGA  TAACCATCTC  GCAAATAAAT  AAGTATTTTA  CTGTTTTCGT                       1636

AACAGTTTTG  TAATAAAAAA  ACCTATAAAT  ATGCCGGATT  ATTCATACCG  TCCCACCATC                       1696

GGGCGTACCT  ACGTGTACGA  CAACAAATAT  TACAAAAATT  TAGGTGCCGT  TATCAAGAAC                       1756

GCTAAGC                                                                                     1763
```

( 2 ) INFORMATION FOR SEQ ID NO:4:

( i ) SEQUENCE CHARACTERISTICS:
        ( A ) LENGTH: 210 amino acids
        ( B ) TYPE: amino acid (D) TOPOLOGY: linear (ii) MOLECULE TYPE: protein (xi) SEQUENCE DESCRIPTION: SEQ ID NO:4:

| Met | Ala | Asn | Ala | Ser | Tyr | Asn | Val | Trp | Ser | Pro | Leu | Ile | Ser | Ala | Ser |
|---|---|---|---|---|---|---|---|---|---|---|---|---|---|---|---|
| 1 | | | | 5 | | | | | 10 | | | | | 15 | |

| Cys | Leu | Asp | Lys | Lys | Ala | Thr | Tyr | Leu | Ile | Asp | Pro | Asp | Phe | Ile |
|---|---|---|---|---|---|---|---|---|---|---|---|---|---|---|
| | | | 20 | | | | | 25 | | | | 30 | | |

| Asp | Lys | Leu | Thr | Leu | Thr | Pro | Tyr | Thr | Val | Phe | Tyr | Asn | Gly | Gly | Val |
|---|---|---|---|---|---|---|---|---|---|---|---|---|---|---|---|
| | | | 35 | | | | 40 | | | | | 45 | | | |

| Leu | Val | Lys | Ile | Ser | Gly | Leu | Arg | Leu | Tyr | Met | Leu | Leu | Thr | Ala | Pro |
|---|---|---|---|---|---|---|---|---|---|---|---|---|---|---|---|
| | 50 | | | | | 55 | | | | | 60 | | | | |

| Pro | Thr | Ile | Asn | Glu | Ile | Lys | Asn | Ser | Asn | Phe | Lys | Lys | Arg | Ser | Lys |
|---|---|---|---|---|---|---|---|---|---|---|---|---|---|---|---|
| 65 | | | | | 70 | | | | | 75 | | | | | 80 |

| Arg | Asn | Ile | Cys | Met | Lys | Glu | Cys | Ala | Glu | Gly | Lys | Lys | Asn | Val | Val |
|---|---|---|---|---|---|---|---|---|---|---|---|---|---|---|---|
| | | | | 85 | | | | | 90 | | | | | 95 | |

| Asp | Met | Leu | Asn | Ser | Lys | Ile | Asn | Met | Pro | Pro | Cys | Ile | Lys | Lys | Ile |
|---|---|---|---|---|---|---|---|---|---|---|---|---|---|---|---|
| | | | 100 | | | | | 105 | | | | | 110 | | |

| Leu | Gly | Asp | Leu | Lys | Glu | Asn | Asn | Val | Pro | Arg | Gly | Gly | Met | Tyr | Arg |
|---|---|---|---|---|---|---|---|---|---|---|---|---|---|---|---|
| | | 115 | | | | | 120 | | | | | 125 | | | |

| Lys | Arg | Phe | Ile | Leu | Asn | Cys | Tyr | Ile | Ala | Asn | Val | Val | Ser | Cys | Ala |
|---|---|---|---|---|---|---|---|---|---|---|---|---|---|---|---|
| | 130 | | | | | 135 | | | | | 140 | | | | |

| Lys | Cys | Glu | Asn | Arg | Cys | Leu | Ile | Asn | Ala | Leu | Thr | His | Phe | Tyr | Asn |
|---|---|---|---|---|---|---|---|---|---|---|---|---|---|---|---|
| 145 | | | | | 150 | | | | | 155 | | | | | 160 |

| His | Asp | Ser | Lys | Cys | Val | Gly | Glu | Val | Met | His | Leu | Leu | Ile | Lys | Ser |
|---|---|---|---|---|---|---|---|---|---|---|---|---|---|---|---|
| | | | | 165 | | | | | 170 | | | | | 175 | |

| Gln | Asp | Val | Tyr | Lys | Pro | Pro | Asn | Cys | Gln | Lys | Met | Lys | Asn | Val | Asp |
|---|---|---|---|---|---|---|---|---|---|---|---|---|---|---|---|
| | | | 180 | | | | | 185 | | | | | 190 | | |

| Lys | Leu | Cys | Pro | Phe | Ala | Gly | Asn | Cys | Lys | Gly | Leu | Asn | Pro | Ile | Cys |
|---|---|---|---|---|---|---|---|---|---|---|---|---|---|---|---|
| | | 195 | | | | | 200 | | | | | 205 | | | |

| Asn | Tyr |
|---|---|
| | 210 |

(2) INFORMATION FOR SEQ ID NO:5:

(i) SEQUENCE CHARACTERISTICS:
        (A) LENGTH: 210 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:5:

| Met | Ala | Asn | Ala | Ser | Tyr | Asn | Val | Trp | Ser | Pro | Leu | Ile | Arg | Ala | Ser |
|---|---|---|---|---|---|---|---|---|---|---|---|---|---|---|---|
| 1 | | | | 5 | | | | | 10 | | | | | 15 | |

| Cys | Leu | Asp | Lys | Lys | Ala | Thr | Tyr | Leu | Ile | Asp | Pro | Asp | Phe | Ile |
|---|---|---|---|---|---|---|---|---|---|---|---|---|---|---|
| | | | 20 | | | | | 25 | | | | 30 | | |

| Asp | Lys | Leu | Thr | Leu | Thr | Pro | Tyr | Thr | Val | Phe | Tyr | Asn | Gly | Gly | Val |
|---|---|---|---|---|---|---|---|---|---|---|---|---|---|---|---|
| | | | 35 | | | | 40 | | | | | 45 | | | |

| Leu | Val | Lys | Ile | Ser | Gly | Leu | Arg | Leu | Tyr | Met | Leu | Leu | Thr | Ala | Pro |
|---|---|---|---|---|---|---|---|---|---|---|---|---|---|---|---|
| | 50 | | | | | 55 | | | | | 60 | | | | |

| Pro | Thr | Ile | Asn | Glu | Ile | Lys | Asn | Ser | Asn | Phe | Lys | Lys | Arg | Ser | Lys |
|---|---|---|---|---|---|---|---|---|---|---|---|---|---|---|---|
| 65 | | | | | 70 | | | | | 75 | | | | | 80 |

| Arg | Asn | Ile | Cys | Met | Lys | Glu | Cys | Val | Glu | Gly | Lys | Lys | Asn | Val | Val |
|---|---|---|---|---|---|---|---|---|---|---|---|---|---|---|---|
| | | | | 85 | | | | | 90 | | | | | 95 | |

```
Asp  Met  Leu  Asn  Asn  Lys  Ile  Asn  Met  Pro  Pro  Cys  Ile  Lys  Lys  Ile
               100                      105                     110

Leu  Asn  Asp  Leu  Lys  Glu  Asn  Asn  Val  Pro  Arg  Gly  Gly  Met  Tyr  Arg
               115                      120                     125

Lys  Arg  Phe  Ile  Leu  Asn  Cys  Tyr  Ile  Ala  Asn  Val  Val  Ser  Cys  Ala
     130                      135                     140

Lys  Cys  Glu  Asn  Arg  Cys  Leu  Ile  Lys  Ala  Leu  Thr  His  Phe  Tyr  Asn
145                      150                     155                          160

His  Asp  Ser  Lys  Cys  Val  Gly  Glu  Val  Met  His  Leu  Leu  Ile  Lys  Ser
               165                      170                     175

Gln  Asp  Val  Tyr  Lys  Pro  Pro  Asn  Cys  Gln  Lys  Met  Lys  Thr  Val  Asp
               180                      185                     190

Lys  Leu  Cys  Pro  Phe  Ala  Gly  Asn  Cys  Lys  Gly  Leu  Asn  Pro  Ile  Cys
               195                      200                     205

Asn  Tyr
210
```

( 2 ) INFORMATION FOR SEQ ID NO:6:

( i ) SEQUENCE CHARACTERISTICS:
        ( A ) LENGTH: 210 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:6:

```
Met  Ala  Asn  Ala  Ser  Tyr  Asn  Val  Trp  Ser  Pro  Leu  Ile  Ser  Ala  Ser
1                   5                        10                     15

Cys  Leu  Asp  Lys  Lys  Ala  Thr  Tyr  Leu  Ile  Asp  Pro  Asp  Asp  Phe  Ile
               20                       25                     30

Asp  Lys  Leu  Thr  Leu  Thr  Pro  Tyr  Thr  Val  Phe  Tyr  Asn  Gly  Gly  Val
               35                       40                     45

Leu  Val  Lys  Ile  Ser  Gly  Leu  Arg  Leu  Tyr  Met  Leu  Leu  Thr  Ala  Pro
     50                       55                     60

Pro  Thr  Ile  Asn  Glu  Ile  Lys  Asn  Ser  Asn  Phe  Lys  Lys  Arg  Ser  Lys
65                       70                     75                          80

Arg  Asn  Ile  Cys  Met  Lys  Glu  Cys  Ala  Glu  Gly  Lys  Lys  Asn  Val  Val
               85                       90                     95

Asp  Met  Leu  Asn  Ser  Lys  Ile  Asn  Met  Pro  Pro  Cys  Ile  Lys  Lys  Ile
               100                      105                     110

Leu  Gly  Asp  Leu  Lys  Glu  Asn  Asn  Val  Pro  Arg  Gly  Gly  Met  Tyr  Arg
               115                      120                     125

Lys  Arg  Phe  Ile  Leu  Asn  Cys  Tyr  Ile  Ala  Asn  Val  Val  Ser  Cys  Ala
     130                      135                     140

Lys  Cys  Glu  Asn  Arg  Cys  Leu  Ile  Asn  Ala  Leu  Thr  His  Phe  Tyr  Asn
145                      150                     155                          160

His  Asp  Ser  Lys  Cys  Val  Gly  Glu  Val  Met  His  Leu  Leu  Ile  Lys  Ser
               165                      170                     175

Gln  Asp  Val  Tyr  Lys  Pro  Pro  Asn  Cys  Gln  Lys  Met  Lys  Asn  Val  Asp
               180                      185                     190

Lys  Leu  Cys  Pro  Phe  Ala  Gly  Asn  Cys  Lys  Gly  Leu  Asn  Pro  Ile  Cys
               195                      200                     205

Asn  Tyr
```

2 1 0

( 2 ) INFORMATION FOR SEQ ID NO:7:

( i ) SEQUENCE CHARACTERISTICS:
        ( A ) LENGTH: 2793 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:7:

```
GTCGACGCGC  TTCTGCGTAT  AATTGCACAC  TAACATGTTG  CCCTTTGAAC  TTGACCTCGA    60
TTGTGTTAAT  TTTTGGCTAT  AAAAAGGTCA  CCCTTTAAAA  TTTGTTACAT  AATCAAATTA   120
CCAGTACAGT  TATTCGGTTT  GAAGCAAAAT  GACTATTCTC  TGCTGGCTTG  CACTGCTGTC   180
TACGCTTACT  GCTGTAAATG  CGGCCAATAT  ATTGGCCGTG  TTTCCTACGC  CAGCTTACAG   240
CCACCATATA  GTGTACAAAG  TGTATATTGA  AGCCCTTGCC  GAAAAATGTC  ACAACGTTAC   300
GGTCGTCAAG  CCCAAACTGT  TGCGTATTC   AACTAAAACT  TATTGCGGTA  ATATCACGGA   360
AATTAATGCC  GACATGTCTG  TTGAGCAATA  CAAAAAACTA  GTGGCGAATT  CGGCAATGTT   420
TAGAAAGCGC  GGAGTGGTGT  CCGATACAGA  CACGGTAACC  GCCGCTAACT  ACCTAGGCTT   480
GATTGAAATG  TTCAAAGACC  AGTTTGACAA  TATCAACGTG  CGCAATCTCA  TTGCCAACAA   540
CCAGACGTTT  GATTTAGTCG  TCGTGGAAGC  GTTTGCCGAT  TATGCGTTGG  TGTTTGGTCA   600
CTTGTACGAT  CCGGCGCCCG  TAATTCAAAT  CGCGCCTGGC  TACGGTTTGG  CGGAAAACTT   660
TGACACGGTC  GGCGCCGTGG  CGCGGCACCC  CGTCCACCAT  CCTAACATTT  GGCGCAGCAA   720
TTTCGACGAC  ACGGAGGCAA  ACGTGATGAC  GGAAATGCGT  TTGTATAAAG  AATTTAAAAT   780
TTTGGCCAAC  ATGTCCAACG  CGTTGCTCAA  ACAACAGTTT  GGACCCAACA  CACCGACAAT   840
TGAAAAACTA  CGCAACAAGG  TGCAATTGCT  TTTGCTAAAC  CTGCATCCCA  TATTTGACAA   900
CAACCGACCC  GTGCCGCCCA  GCGTGCAGTA  TCTTGGCGGA  GGAATCCATC  TTGTAAAGAG   960
CGCGCCGTTG  ACCAAATTAA  GTCCGGTCAT  CAACGCGCAA  ATGAACAAGT  CAAAAAGCGG  1020
AACGATTTAC  GTAAGTTTTG  GGTCGAGCAT  TGACACCAAA  TCGTTTGCAA  ACGAGTTTCT  1080
TTACATGTTA  ATCAATACGT  TCAAAACGTT  GGATAATTAC  ACCATATTAT  GGAAAATTGA  1140
CGACGAAGTA  GTAAAAAACA  TAACGTTGCC  CGCCAACGTA  ATCACGCAAA  ATTGGTTTAA  1200
TCAACGCGCC  GTGCTGCGTC  ATAAAAAAAT  GGCGGCGTTT  ATTACGCAAG  GCGGACTACA  1260
ATCGAGCGAC  GAGGCCTTGG  AAGCCGGGAT  ACCCATGGTG  TGTCTGCCCA  TGATGGGCGA  1320
CCAGTTTTAC  CATGCGCACA  AATTACAGCA  ACTCGGCGTA  GCCCGCGCCT  GGACACTGT   1380
TACCGTTTCC  AGCGATCAAC  TACTAGTGGC  GATAAACGAC  GTGTTGTTTA  ACGCGCCTAC  1440
CTACAAAAAA  CACATGGCCG  AGTTATATGC  GCTCATCAAT  CATGATAAAG  CAACGTTTCC  1500
GCCTCTAGAT  AAAGCCATCA  AATTCACAGA  ACGCGTAATT  CGATATAGAC  ATGACATCAG  1560
TCGTCAATTG  TATTCATTAA  AAACAACAGC  TGCCAATGTA  CCGTATTCAA  ATTACTACAT  1620
GTATAAATCT  GTGTTTTCTA  TTGTAATGAA  TCACTTAACA  CACTTTTAAT  TACGTCAATA  1680
AATGTTATTC  ACCATTATTT  ACCTGGTTTT  TTTGAGAGGG  CTTTGTGCG   ACTGCGCACT  1740
TCCAGCCTTT  ATAAACGCTC  ACCAACCAAA  GCAGGTCATT  ATTGTGCCAG  GACGTTCAAA  1800
GGCGAAACAT  CGAAATGGAG  TCTGTTCAAA  CGCGCTTATG  TGCCAGTAGC  AATCAATTTG  1860
CTCCGTTCAA  AAAGCGCCAG  CTTGCCGTGC  CGGTCGGTTC  TGTGAACAGT  TTGACACACA  1920
```

-continued

```
CCATCACCTC CACCACCGTC ACCAGCGTGA TTCCAAAAAA TTATCAAGAA AAACGTCAGA      1980

AAATATGCCA CATAATATCT TCGTTGCGTA ACACGCACTT GAATTTCAAT AAGATACAGT      2040

CTGTACATAA AAAGAAACTG CGGCATTTGC AAAATTTGCT AAGAAAAAG AACGAAATTA       2100

TTGCCGAGTT GGTTAGAAAA CTTGAAAGTG CACAGAAGAA GACAACGCAC AGAAATATTA      2160

GTAAACCAGC TCATTGGAAA TACTTTGGAG TAGTCAGATG TGACAACACA ATTCGCACAA      2220

TTATTGGCAA CGAAAAGTTT GTAAGGAGAC GTTTGGCCGA GCTGTGCACA TTGTACAACG      2280

CCGAGTACGT GTTTTGCCAA GCACGCGCCG ATGGAGACAA AGATCGACAG GCACTAGCGA      2340

GTCTGCTGAC GGCGGCGTTT GGTTCGCGAG TCATAGTTTA TGAAAATAGT CGCCGGTTCG      2400

AGTTTATAAA TCCGGACGAG ATTGCTAGTG GTAAACGTTT AATAATTAAA CATTTGCAAG      2460

ATGAATCTCA AAGTGATATT AACGCCTATT AATTTGAAAG GTGAGGAAGA GCCCAATTGC      2520

GTTGAGCGCA TTACCATAAT GCCATGTATT TTAATAGATA CTGAGATCTG TTTAAATGTC      2580

AGATGCCGTT CTCCTTTTGC CAAATTCAAA GTATTGATTA TTGTAGATGG CTTTGATAGC      2640

GCTTATATTC AGGCTACCTT TTGTAGCATT AGCGATAGTG TAACAATTGT TAACAAATCT      2700

AACGAAAAGC ATGTAACGTT TGACGGGTTT GTAAGGCCGG ACGATGAAGG TACAACAATG      2760

CCTTATGTCA TTGGACCATT ATATTCTGTC GAC                                  2793
```

( 2 ) INFORMATION FOR SEQ ID NO:8:

( i ) SEQUENCE CHARACTERISTICS:
        ( A ) LENGTH: 341 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:8:

```
TGAGACGCAC AAACTAATAT CACAAACTGG AAATGTCTAT CAATATATAG TTGCTGATAT       60

CATGGAGATA ATTAAAATGA TAACCATCTC GCAAATAAAT AAGTATTTTA CTGTTTTCGT      120

AACAGTTTTG TAATAAAAAA ACCTATAAAT ATGCCGGATT ATTCATACCG TCCCACCATC      180

GGGCGTACCT ACGTGTACGA CAACAAGTAC TACAAAAATT TAGGTGCCGT TATCAAGAAC      240

GCTAAGCGCA AGAAGCACTT CGCCGAACAT GAGATCGAAG AGGCTACCCT CGACCCCCTA      300

GACAACTACC TAGTGGCTGA GGATCCTTTC CTGGGACCCG G                         341
```

( 2 ) INFORMATION FOR SEQ ID NO:9:

( i ) SEQUENCE CHARACTERISTICS:
        ( A ) LENGTH: 351 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:9:

```
TGAAACGCAC AAACTAATAT TACACACTAA AAATGTCTAT CATTTCGGCT TAATATATAG       60

TTGCTGATAT TATGTAAATA ATTAAAATGA TAACCATCTC GCAAATAAAT AAGTATTTTA      120

CTGTTTTCGT AACAGTTTTG TAATAAAAAA ACCTATAAAT ATGCCGGATT ATTCATACCG      180

TCCCACCATC GGGCGTACCT ACGTGTACGA CAACAAATAT TACAAAAATT TAGGTGCCGT      240
```

```
TATCAAGAAC   GCTAAGCGCA   AGAAGCACTT   CGCCGAACAT   GAGATCGAAG   AGGCTACCCT        300

CGACCCCCTA   GACAACTACC   TAGTGGCTGA   GGATCCTTTC   CTGGGACCCG   G                 351
```

( 2 ) INFORMATION FOR SEQ ID NO:10:

( i ) SEQUENCE CHARACTERISTICS:
        ( A ) LENGTH: 351 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:10:

```
TGAAACGCAC   AAACTAATAT   TACACACTAA   AAAAATCTAT   CATTTCGGCT   TAATATATAG        60

TTGCTGATAT   TATGTAAATA   ATTAAAATGA   TAACCATCTC   GCAAATAAAT   AAGTATTTTA        120

CTGTTTTCGT   AACAGTTTTG   TAATAAAAAA   ACCTATAAAT   ATGCCGGATT   ATTCATACCG        180

TCCGACCATC   GGGCGTACCT   ACGTGTACGA   CAACAAATAT   TACAAAAACT   TGGGTTCTGT        240

TATTAAAAAC   GCCAAGCGCA   AGAAGCACCT   AATCGAACAT   GAAGAAGAGG   AGAAGNACTT        300

GGATCCCTTA   GACAATTACA   TGGTTGCCNN   AGATCCTTTT   CTAGGACCTG   G                 351
```